United States Patent
Kachlany

(10) Patent No.: US 8,926,990 B2
(45) Date of Patent: Jan. 6, 2015

(54) TREATMENT AND DIAGNOSIS OF INFLAMMATORY DISORDERS AND HIV

(75) Inventor: Scott C. Kachlany, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/446,949

(22) Filed: Apr. 13, 2012

(65) Prior Publication Data

US 2012/0263644 A1 Oct. 18, 2012

Related U.S. Application Data

(63) Continuation-in-part of application No. PCT/US2010/052453, filed on Oct. 13, 2010, and a continuation-in-part of application No. PCT/US2010/056864, filed on Nov. 16, 2010.

(60) Provisional application No. 61/251,171, filed on Oct. 13, 2009, provisional application No. 61/285,378, filed on Dec. 10, 2009, provisional application No. 61/261,984, filed on Nov. 17, 2009.

(51) Int. Cl.
| | | |
|---|---|---|
| *A61K 39/02* | (2006.01) | |
| *A61K 39/00* | (2006.01) | |
| *A61K 38/00* | (2006.01) | |
| *C07K 1/00* | (2006.01) | |
| *G01N 33/50* | (2006.01) | |
| *A61K 38/16* | (2006.01) | |
| *A61K 45/06* | (2006.01) | |
| *G01N 33/569* | (2006.01) | |

(52) U.S. Cl.
CPC .......... *G01N 33/5052* (2013.01); *A61K 38/164* (2013.01); *A61K 45/06* (2013.01); *G01N 33/56911* (2013.01); *G01N 2800/709* (2013.01); *G01N 33/56988* (2013.01); *G01N 2800/26* (2013.01); *G01N 2800/52* (2013.01); *G01N 2800/7095* (2013.01); *Y10S 530/825* (2013.01)
USPC .................. 424/236.1; 424/234.1; 424/184.1; 424/190.1; 514/1.1; 530/350; 530/825

(58) Field of Classification Search
None
See application file for complete search history.

(56) References Cited

U.S. PATENT DOCUMENTS

2005/0032217 A1* 2/2005 Zadeh .......................... 435/455

OTHER PUBLICATIONS

Dileepan et al. Infect. Immun. 75: 4851-4856, Jul. 16, 2007.*
Kachlany, S. C. et al., 2010. "Anti-leukemia activity of a bacterial toxin with natural specificity for LFA-1 on white blood cells", Leukemia Research 34:777-85.
DesJardin et al. "Mycobacterium tuberculosis-infected human macrophages exhibit enhanced cellular adhesion with increased expression of LFA-1 and ICAM-1 and reduced expression and/or function of complement receptors, FcgammaRII and the mannose receptor", Microbiology 2002; 148: 3161-3171.
Guttman-Yassky et al. 2008. "Blockade of CD11 a by efalizumab in psoriasis patients induces a unique state of T-cell hyporesponsiveness", The Journal of Investigative Dermatology, 128(5): 1182-1191.
P. Giblin et al. 2006. "LFA-1 as a Key Regulator of Immune Function: Approaches toward the Development of LFA-1-Based Therapeutics", Current Pharmaceutical Design 12(22): 2771-2795.
Shamik Ghosh et al. 2006. "The LFA-1 adhesion molecule is required for protective immunity during pulmonary *Mycobacterium tuberculosis* infection", The Journal of Immunology 176(8): 4914-4922.

* cited by examiner

*Primary Examiner* — S. Devi
(74) *Attorney, Agent, or Firm* — Fox Rothschild LLP

(57) ABSTRACT

This invention concerns compositions and methods of treating or diagnosing inflammatory disorders and other disorders, as well as compositions and methods of treating HIV.

4 Claims, 22 Drawing Sheets

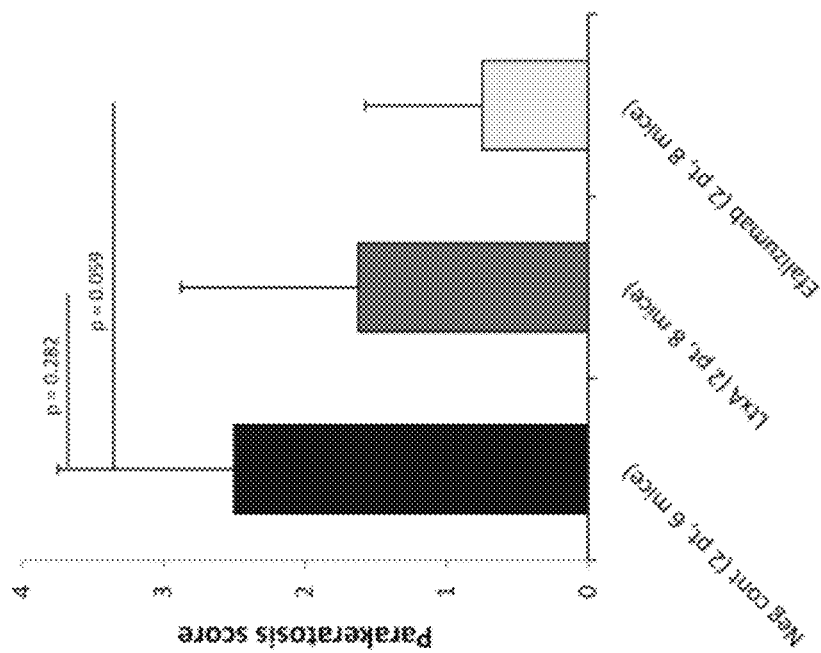
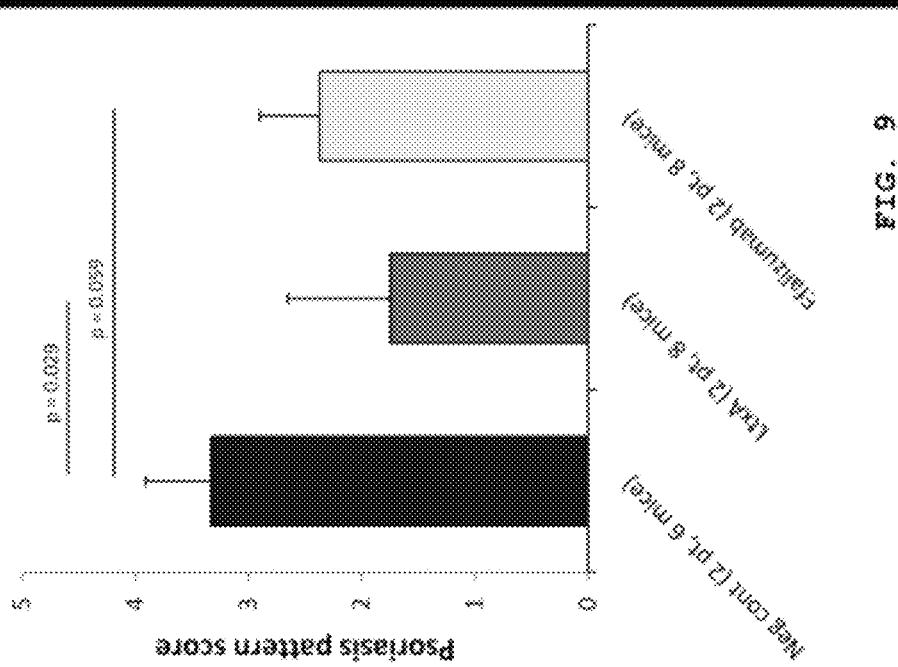
FIG. 9

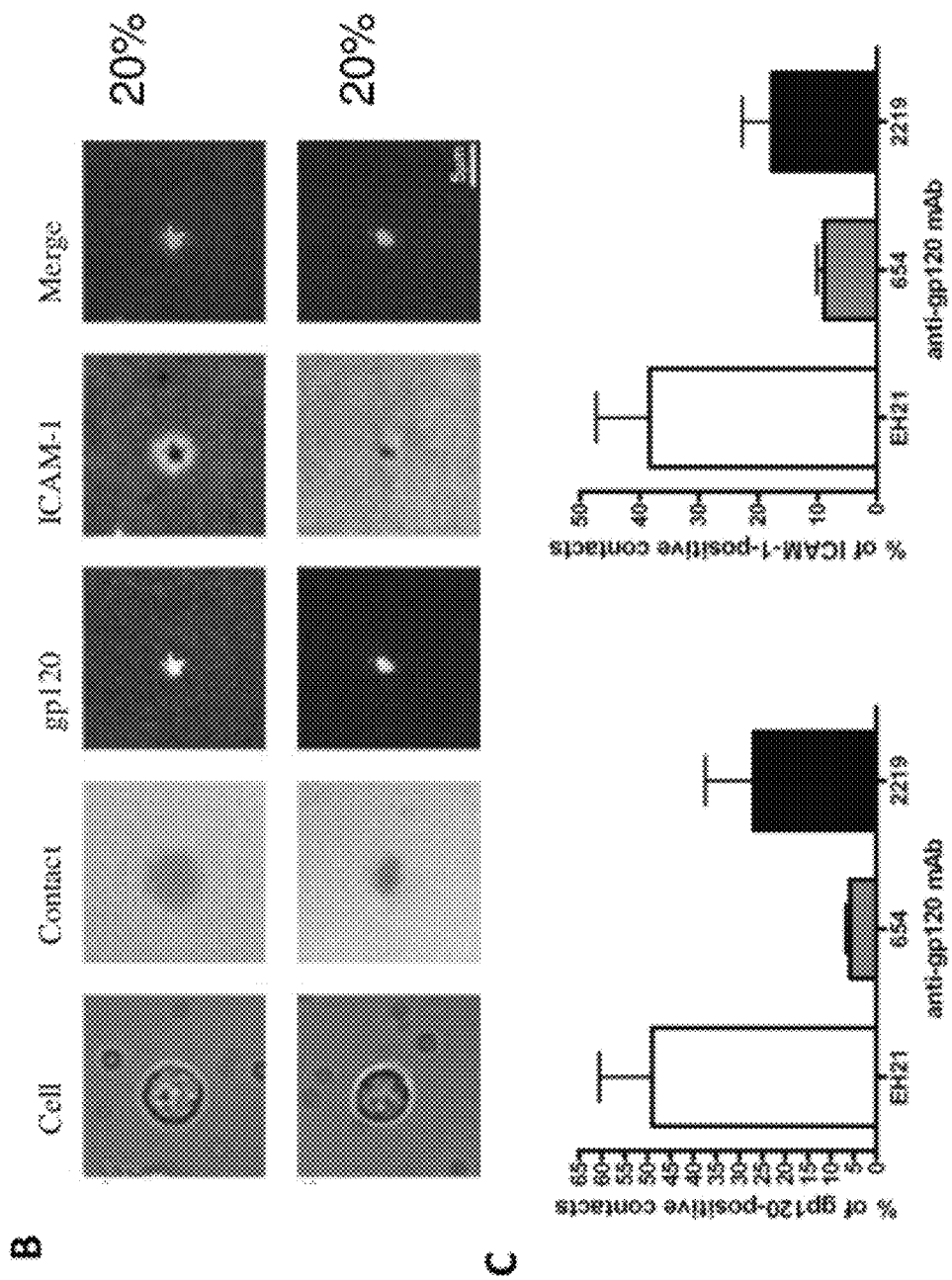
FIG. 16B and C

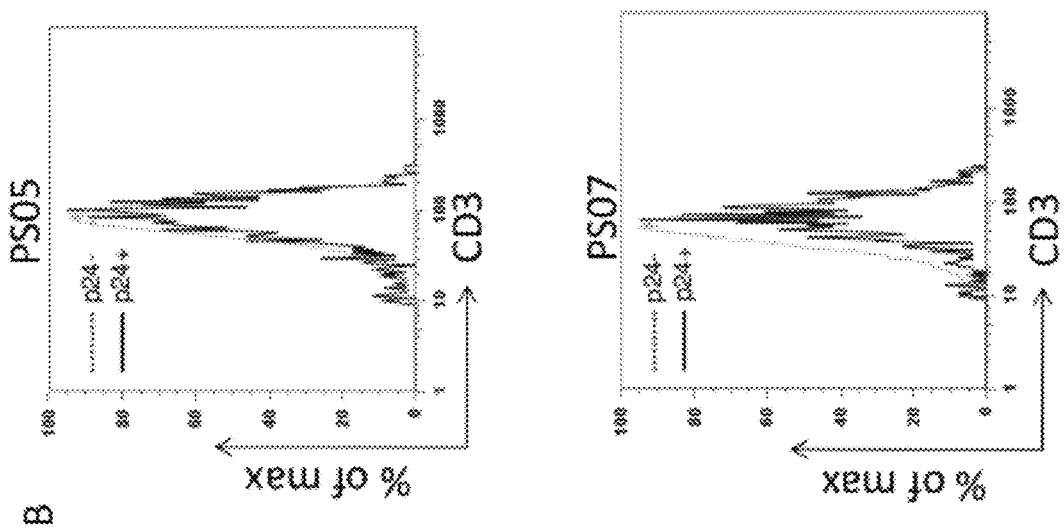
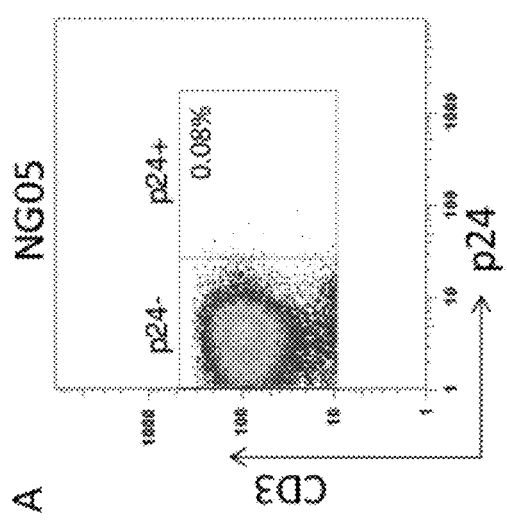
FIG. 21

TREATMENT AND DIAGNOSIS OF INFLAMMATORY DISORDERS AND HIV

CROSS REFERENCE TO RELATED APPLICATIONS

This application is a continuation-in-part of International Application No. PCT/US10/52453 filed Oct. 13, 2010, which, in turn claims priority under 35 U.S.C. §119(e) of U.S. Provisional Application Nos. 61/251,171, filed Oct. 13, 2009 and 61/285,378, filed Dec. 10, 2009. This application is also a continuation-in-part of International Application No. PCT/US10/56864, filed Nov. 16, 2010, which claims priority under 35 U.S.C. §119(e) to U.S. Provisional Application No. 61/261,984, filed Nov. 17, 2009. The contents of all five applications are incorporated herein by reference in their entirety.

GOVERNMENT INTERESTS

The invention disclosed herein was made, at least in part, with Government support under Grant No. NIH R01DE16131 and Grant No. NIH R01DE16133 from the National Institutes of Health. Accordingly, the U.S. Government has certain rights in this invention.

FIELD OF THE INVENTION

This invention relates to reagents and methods for treating or diagnosing inflammatory disorders and other disorders, as well as to reagents and methods for removing HIV-infected cells from a subject and, thereby, treating HIV infection.

BACKGROUND OF THE INVENTION

Inflammatory disorders are disorders characterized by the abnormal activation and subsequent migration of white blood cells (WBCs) to affected areas of the body. These conditions encompass a wide range of ailments that affect the lives of millions of people throughout the world. Although some treatments are presently available, many possess significantly side effects or are not very effective in alleviating all symptoms. At the same time, few tests exist that reliably diagnose or monitor the progress of the diseases. Thus, there is a need for drugs and reagents for treatment and diagnosis of inflammatory disorders.

Human immunodeficiency virus (HIV) is a lentivirus that causes acquired immunodeficiency syndrome (AIDS), a condition in humans characterized by several clinical features including wasting syndromes, central nervous system degeneration and profound immunosuppression that results in life-threatening opportunistic infections and malignancies. Two closely related types of HIV, i.e., HIV-1 and HIV-2, have been identified. Of them, HIV-1 is the most common cause of AIDS. Current efforts to treat HIV infection and prevent HIV transmission have focused on antiretroviral therapy (ART) and topical microbicides that kill the virus at the primary entry points or on vaccines that elicit virus-neutralizing antibodies. These strategies target the virus directly. However, given the tremendous genetic and antigenic variability and the high mutation rates of HIV-1, designing vaccines and drugs that are effective against diverse virus isolates circulating worldwide today has been a formidable challenge. Thus, there is as need for novel therapeutic agents and methods for treatment or inhibition of HIV infection.

SUMMARY OF THE INVENTION

This invention relates to treatment and diagnosis of inflammatory disorders, e.g., autoimmune diseases, using leukotoxin (LtxA), a bacterial protein, as well as to compositions and methods to treat, reduce and prevent HIV infection using LtxA. Shown below are the polypeptide and nucleotide sequences of LtxA.

*Aggregatibacter actinomycetemcomitans*
strain NJ4500 protein sequence (SEQ ID NO: 1)

```
MATTSLLNTKQQAAQFANSVADRAKENIDAAKEQLQKALDKLGKTGKKLTLYIKNYKKGN

GLTALIKAAQKLGIEVYHEGKDGPALTNGILNTGKKLLGLTERGLTLFAPELDKWIQGNK

HLSNSVGSTGNLTKAIDKVQSVLGTLQAFLNTAFSGMDLDALIKARQNGKNVTDVQLAKA

SLNLINELIGTISSITNNVDTFSKQLNKLGEALGQVKHFGSFGDKLKNLPKLGNLGKGLG

ALSGVLSAISAALLLANKDADTATKAAAAAELTNKVLGNIGKAITQYLIAQRAAAGLSTT

GPVAGLIASVVSLAISPLSFLGIAKQFDRARMLEEYSKRFKKFGYNGDSLLGQFYKNTGI

ADAAITTINTVLSAIAAGVGAASAGSLVGAPIGLLVSAITSLISGILDASKQAVFEHIAN

QLADKIKAWENKYGKNYFENGYDARHSAFLEDSLKLFNELREKYKTENILSITQQGWDQR

IGELAGITRNGDRIQSGKAYVDYLKKGEELAKHSDKFTKQILDPIKGNIDLSGIKGSTTL

TFLNPLLTAGKEERKTRQSGKYEFITELKVKGRTDWKVKGVPNSNGVYDFSNLIQHAVTR

DNKVLEARLIANLGAKDDYVFVGSGSTIVNAGDGYDVVDYSKGRTGALTIDGRNATKAGQ

YKVERDLSGTQVLQETVSKQETKRGKVTDLLEYRNYKLDYYYTNKGFKAHDELNSVEEII

GSTLRDKFYGSKFNDVFHGHDGDDLIYGYDGDDRLYGDNGNDEIHGGQGNDKLYGGAGND

RLFGEYGNNYLDGGEGDDHLEGGNGSDILRGGSGNDKLFGNQGDDLLDGGEGDDQLAGGE

GNDIYVYRKEYGHHTITEHSGDKDKLSLANINLKDVSFERNGNDLLLKTNNRTAVTFKGW
```

-continued

FSKPNSSAGLDEYQRKLLEYAPEKDRARLKRQFELQRGKVDKSLNNKVEEIIGKDGERIT

SQDIDNLFDKSGNKKTISPQELAGLIKNKGKSSSLMSSSRSSSMLTQKSGLSNDISRIIS

ATSGFGSSGKALSASPLQTNNNFNSYANSLATTAA

*Aggregatibacter actinomycetemcomitans*
strain NJ4500 DNA sequence
(SEQ ID NO: 2)

ATGGCAACTACTTCACTGCTAAATACAAAACAGCAAGCTGCACAGTTTGCAAATTCAGTT

GCAGATAGAGCTAAGGAAAATATTGATGCTGCAAAAGAACAATTGCAAAAGGCGTTAGAT

AAATTAGGGAAGACAGGTAAGAAATTAACTTTATATATCCCTAAGAATTACAAAAAAGGA

AATGGTCTTACTGCGCTTATAAAAGCAGCACAGAAGTTAGGGATTGAAGTATATCATGAA

GGGAAAGACGGCCCGGCATTAACTAATGGTATTTTAAATACTGGGAAAAAATTACTTGGT

CTTACCGAACGAGGTTTAACTTTATTTGCTCCGGAATTAGATAAATGGATTCAAGGTAAT

AAACATTTAAGTAATTCTGTGGGTAGTACTGGAAATTTGACAAAAGCGATAGATAAGGTT

CAGAGTGTTCTTGGTACGTTACAAGCGTTTTTGAACACCGCATTTTCGGGCATGGATTTA

GATGCCTTAATTAAAGCCCGTCAAAATGGTAAAAATGTAACAGATGTACAGCTAGCAAAA

GCCAGTCTTAACCTGATTAATGAATTGATTGGTACTATTTCTAGCATTACAAATAATGTA

GATACTTTTTCTAAACAACTTAATAAGTTAGGTGAAGCACTAGGACAAGTAAAACATTTT

GGTAGTTTTGGAGATAAATTAAAGAATTTACCTAAGTTAGGTAATCTTGGAAAAGGTTTA

GGTGCATTATCCGGTGTATTGTCGGCTATATCAGCGGCTCTATTACTTGCAAATAAAGAT

GCTGATACTGCAACGAAAGCAGCGGCTGCAGCTGAATTGACAAATAAAGTGCTAGGTAAC

ATCGGTAAAGCGATCACACAATACTTGATTGCTCAACGTGCTGCAGCGGGcTTTCTACT

ACGGGACCTGTCGCAGGGTTAATTGCCTCTGTGGTCAGCTTGGCAATCAGCCCTTTGTCT

TTCCTAGGTATTGCGAAACAATTTGATCGTGCGAGAATGCTTGAGGAATACTCGAAACGC

TTTAAGAAATTTGGTTATAACGGCGATAGTTTACTTGGTCAATTCTACAAAAATACAGGG

ATCGCAGATGCTGCGATTACAACGATTAACACTGTATTAAGTGCTATTGCAGCAGGGGTT

GGTGCAGCCTCCGCCGGTTCTTTAGTTGGTGCGCCAATCGGTTTGTTAGTGAGTGCGATT

ACCAGCTTAATTTCAGGAATTCTTGATGCTTCTAAACAAGCCGTTTTTGAACATATCGCG

AATCAGCTCGCCGATAAAATTAAAGCATGGGAGAATAAGTACGGTAAGAATTACTTTGAA

AATGGCTATGATGCCCGTCATTCCGCCTTCTTGGAAGATTCACTAAAATTATTTAATGAG

TTACGTGAAAAATATAAAACCGAAAATATATTATCTATCACTCAACAAGGTTGGGATCAG

CGCATTGGTGAATTAGCAGGTATCACTCGTAATGGAGATCGTATTCAAAGTGGTAAAGCT

TATGTGGATTATTTGAAAAAGGGTGAGGAGCTTGCAAAGCATAGCGATAAATTCACTAAA

CAGATTTTAGATCCAATCAAAGGTAATATTGATCTTTCGGGTATaAAAGGTTCTACCACT

CTAACTTTTTTAAATCCGTTGTTAACCGCAGGTAAGGAAGAACGGAAAACACGTCAGTCA

GGTAAATATGAATTTATTACTGAATTAAAAGTAAAAGGACGTACCGATTGGAAGGTAAAA

GGTGTTCCTAATTCTAATGGTGTATATGATTTTTCTAACTTAATTCAACATGCCGTTACA

CGTGATAATAAAGTTCTAGAAGCAAGATTAATTGCTAATTTGGGTGCTAAAGATGATTAT

GTTTTTGTCGGATCCGGTTCAACAATAGTTAATGCTGGAGACGGTTATGATGTGGTGGAC

TATAGTAAAGGTCgCACCGGTGCATTAACAATCGACGGTCGTAATGCTACTAAAGCCGGA

CAATATAAGGTTGAAAGAGATCTTAGCGGTACTCAAGTCTTGCAGGAAACCGTATCAAAG

CAAGAAACTAAACGAGGGAAGGTTACCGATCTACTTGAATATCGTAACTATAAATTAGAT

TACTATTATACGAATAAGGGCTTTAAAGCTCATGATGAATTAAACTCAGTAGAGGAAATT

```
-continued
ATCGGCAGCACACTACGTGATAAATTTTATGGTTCTAAATTTAATGATGTTTTCCATGGT

CACGATGGCGATGATTTGATTTATGGTTATGATGGCGATGATCGTTTGTATGGCGATAAT

GGGAATGACGAAATTCATGGCGGCCAAGGTAATGATAAGCTCTATGGTGGTGCCGGTAAC

GATAGGCTCTTTGGTGAATATGGCAACAACTATCTTGACGGTGGAGAAGGCGACGACCAC

TTAGAGGGAGGCAATGGTTCCGATATTCTAAGAGGTGGAAGTGGCAATGATAAGTTGTTT

GGAAACCAAGGAGATGATTTACTTGACGGTGGAGAAGGCGATGACCAACTTGCCGGTGGA

GAAGGAAATGATATTTATGTTTACCGTAAAGAATATGGGCACCACACTATTACGGAACAT

AGCGGTGATAAAGATAAATTATCATTAGCAAATATCAATCTCAAAGATGTGTCATTTGAG

CGTAACGGCAATGATCTACTATTGAAAACAAATAATAGAACAGCAGTAACATTTAAAGGA

TGGTTTAGTAAACCTAATTCATCGGCAGGATTAGATGAGTATCAAAGAAAACTTCTTGAA

TACGCACCTGAAAAGGATCGTGCACGACTTAAGAGACAATTTGAGTTACAGCGAGGTAAA

GTCGACAAATCACTCAATAATAAAGTTGAAGAAATTATCGGTAAAGATGGGGAGCGGATT

ACTTCGCAAGACATTGATAATCTTTTTGATAAGAGTGGGAACAAAAAGACAATTTCACCT

CAAGAGCTTGCCGGACTTATTAAGAATAAAGGTAAGTCAAGTAGCCTTATGTCTTCTTCT

CGTTCGTCAAGTATGCTTACACAAAAGTCCGGTTTGTCAAATGATATTAGTCGTATTATT

TCAGCAACCAGTGGTTTTGGTTCATCCGGTAAAGCGTTATCCGCTTCGCCATTGCAGACC

AATAATAACTTTAACTCTTACGCAAATTCGTTAGCAACTACTGCGGCC
```

One aspect of this invention feature a method for treating an inflammatory disorder or tuberculosis, comprising administering to a subject in need thereof an effective amount of leukotoxin. The leukotoxin can be prepared from *Aggregatibacter actinomycetemcomitans*. In one embodiment, the leukotoxin comprises, consists essentially of, or consists of the sequence of SEQ ID NO: 1. The inflammatory disorder can be an autoimmune disease. Examples of the autoimmune disease include psoriasis, Crohn's disease, ulcerative colitis, rheumatoid arthritis, psoriatic arthritis, multiple sclerosis, lupus, type I diabetes, primary biliary cirrhosis, an inflammatory bowel disease, and transplant rejection. In a prefer embodiment, the disorder is psoriasis.

A second aspect of this invention features a pharmaceutical composition, comprising a leukotoxin and a pharmaceutical carrier for topical application. The leukotoxin can be prepared from *Aggregatibacter actinomycetemcomitans*. In one embodiment, the leukotoxin comprises or consists of the sequence of SEQ ID NO: 1. This composition can be used in treating inflammatory disorders, in particular, those in the skin.

A third aspect of the invention features a diagnosing method for determining whether a subject has an inflammatory disorder, including an autoimmune disease (e.g., psoriasis). The method includes the steps of obtaining from the subject a test sample that contains white blood cells; contacting the sample with leukotoxin (e.g., SEQ ID NO: 1); and determining the percentage of the white blood cells that bind to the leukotoxin in the sample. The subject is determined to have the disorder if the percentage is at or above a predetermined value. The leukotoxin can be labeled with a detectable agent, such as FITC. The sample can be a blood sample or a biopsy sample. Preferably, the contacting step is conducted at 0-4° C., such as about 0° C. The predetermined value can be one obtained from a control subject that does not have the disorder.

A fourth aspect of the invention features a method for determining the effectiveness of a treatment in a patient suffering from an inflammatory disorder, such as an autoimmune disease (e.g., psoriasis). The method include steps of obtaining a sample that contains white blood cells from a patient that has received a treatment; contacting the sample with leukotoxin (e.g., SEQ ID NO: 1); and determining the percentage of the white blood cells that bind to the leukotoxin in the sample. The treatment is determined to be effective if the percentage is below a predetermined value. Like that in the above-mentioned diagnosing method, the leukotoxin can be labeled with a detectable agent (e.g., FITC); the sample can be a blood sample or a biopsy sample. Also, the contacting step can be conducted at 0-4° C., such as at about 0° C. Here, the predetermined value can be a control value obtained from the patient prior to the treatment.

A fifth aspect of this invention features a method to reduce HIV infected cells in a subject. The method includes identifying a subject having an HIV-infection, and reducing the level of cells expressing activated LFA-1 using an anti-LFA-1 agent, wherein the anti-LFA-1 agent is a leukotoxin or an antibody. Another aspect of this invention features a method for inhibiting an infection with HIV in a subject in need thereof, the method includes identifying a subject at risk of, or suspected of, having an HIV-infection, and reducing the level of cells expressing activated LFA-1 in the subject, using an anti-LFA-1 agent, wherein the anti-LFA-1 agent is a leukotoxin or an antibody, and reducing the level of cells expressing activated LFA-1 in the subject. Another aspect of this invention features a method for treating a subject with an HIV infection comprising administering to a subject in need thereof a pharmaceutical composition comprising a therapeutically effective amount of an anti-LFA-1 agent, wherein the anti-LFA-1 agent is a leukotoxin or an antibody and reducing the level of cells expressing activated LFA-1 in the subject. In the aforementioned methods, the cells include HIV-infected cells or the cells are subject to HIV-infection. Examples of such cells include, but not limited to, peripheral blood mononuclear cells (PBMCs) and CD4+ cells. The reducing step can be conducted by contacting the cells with an anti-LFA-1 agent, i.e., an agent that specifically binds to and causes death of the cells expressing activated LFA-1. Examples of the anti-LFA-1 agent include a leukotoxin or an antibody. The leukotoxin can be prepared from *Aggregatibacter actinomycetemcomitans*. In one embodiment, the leukotoxin comprises, consists essentially of, or consists of the sequence of SEQ ID NO: 1. The antibody can be one that specifically binds to activated LFA-1 and is conjugated with a cytotoxic agent.

The term "cytotoxic agent" refers to a substance that inhibits or prevents the function of cells and/or causes destruction of cells. Examples include a radioisotope, a toxin, as chemotherapeutic agent, a drug, or a growth inhibitory agent. Examples of the toxin include small molecule toxins or enzymatically active toxins of bacteria (e.g., diptheria toxin, *Pseudomonas* endotoxin and exotoxin, *Staphylococcal* enterotoxin A), fungi (e.g., α-sarcin, restrictocin), or plant (e.g., abrin, ricin, modeccin, viscumin, pokeweed anti-viral protein, saporin, gelonin, momoridin, trichosanthin, and barley toxin).

In the aforementioned methods, the cells can be contacted with the anti-LFA-1 agent ex vivo or in vivo. In the latter approach, the anti-LFA-1 agent can be administered to the subject in a pharmaceutical composition comprising the anti-LFA-1 agent and a pharmaceutically acceptable carrier. The composition can be administered orally, intravenously, intramuscularly, transdermally, intrarectally, or intravaginally.

Each of the aforementioned methods can further include administering the subject an anti-HIV agent selected from the group consisting of a nucleoside and nucleotide reverse transcriptase inhibitor, a non-nucleoside reverse transcriptase inhibitor, a protease inhibitor, an integrase inhibitor, an entry inhibitor, and a maturation inhibitor. In one embodiment, the anti-HIV agent is selected from the group consisting of AZT, dideoxycytidine, dideoxyinosine, raltegravir, maraviroc, bestatin, hCG, levamisole, estrogen, efavirenz, etravirine, indo-methacin, emtricitabine, tenofovir disoproxil fumarate, amprenavir, tipranavir, indinavir, ritonavir, darunavir, enfuvirtide, and gramicidin. Each of the method can also further include a step at determining the level of HIV-infected cells or cells expressing activated LFA-1 in the subject prior to or after the contacting/administering step.

A sixth aspect of this invention features a composition, e.g., a pharmaceutical composition, that contains the above-mentioned anti-LFA-1 agent such as an antibody or LtxA, an anti-HIV agent, and a pharmaceutically acceptable carrier. The composition can be used for the treatment of an HIV infection in a subject or in the manufacture of a medicament for the treatment of HIV infection.

Specific preferred embodiments of the present invention are described in the following embodiments and claims.

DESCRIPTION OF DRAWINGS

FIG. 9 is a set of diagrams showing effects of LtxA and Efalizumab on psoriasis pattern scores and parakeratosis scores in the psoriasis xenograft transplantation models.

FIGS. 16A-16C are photographs and diagrams showing that HIV gp120 interaction with quiescent naïve CD4 T cells triggers LFA-1 activation and supramolecular rearrangement. FIG. 16A is a set of photographs for one representative cell to show dynamics of quiescent naïve CD4 T cells interaction with HIV gp120 (top and bottom panels) and ICAM-1 (middle and bottom panels) over time. FIG. 16B is a set of photographs showing morphology of ICAM-1 contact areas made upon the interaction of naïve CD4 T cells with gp120 and ICAM-1. Images of representative cells and the percentages of cells that form symmetrical (top panel) or asymmetrical (bottom panel) ICAM-1 rings are shown. FIG. 16C is a set of diagrams showing percentages of cells making gp120-positive (left) and ICAM-1-positive (right) contacts out of the total number of cells seen in fields, representing the averages +/– SEM of three independent experiments.

FIGS. 21A and 21B are diagrams showing the background p24 staining of CD4 T cells (CD3+ CD8−) from a HIV-serongeative donor, NG05 (A), and CD3 expression on and p24+ and p24− CD4 cell populations from HIV-infected subjects PS05 and PS07 (B).

DETAILED DESCRIPTION OF THE INVENTION

Figure 1A:
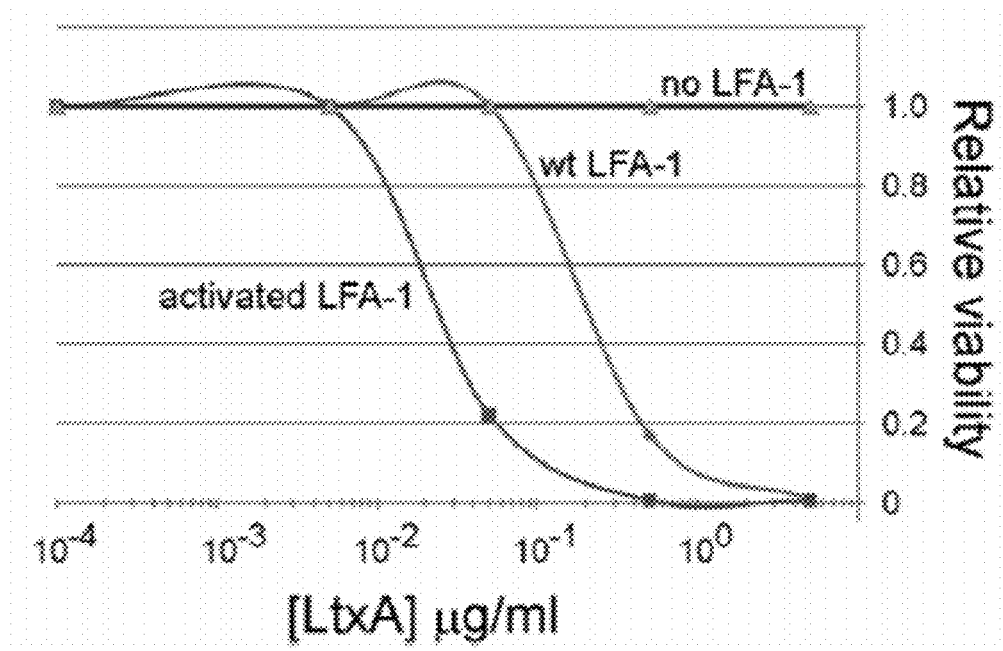
FIG. 1 is a set of diagrams showing sensitivity of Jurkat-derived cells (A) and PBMCs (B) to LtxA-mediated cytotoxicity.
Figure 1B:
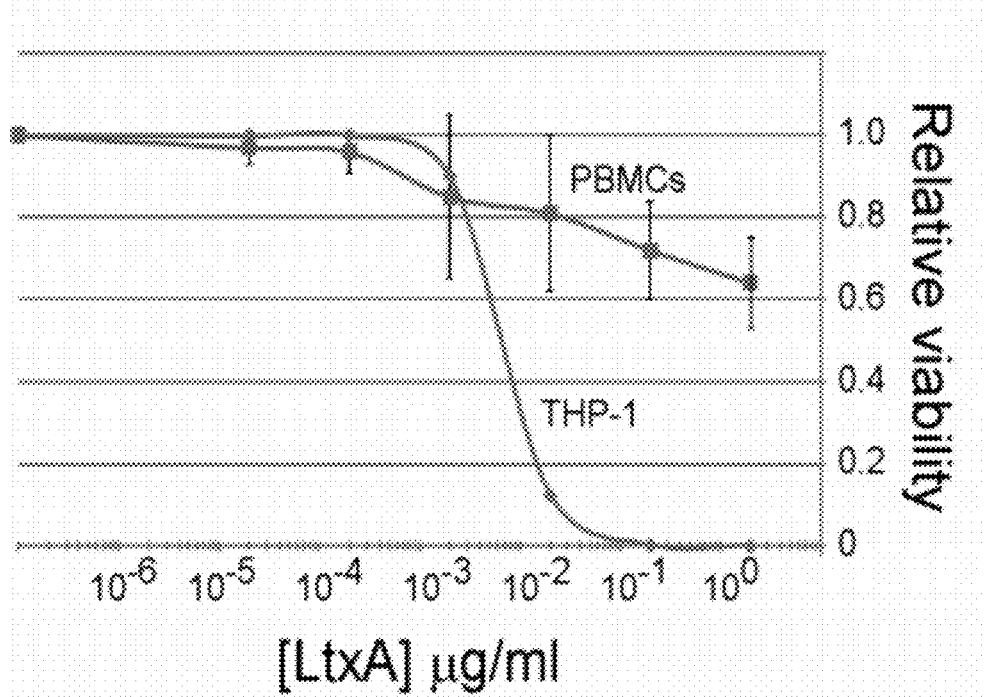
Figure 2:
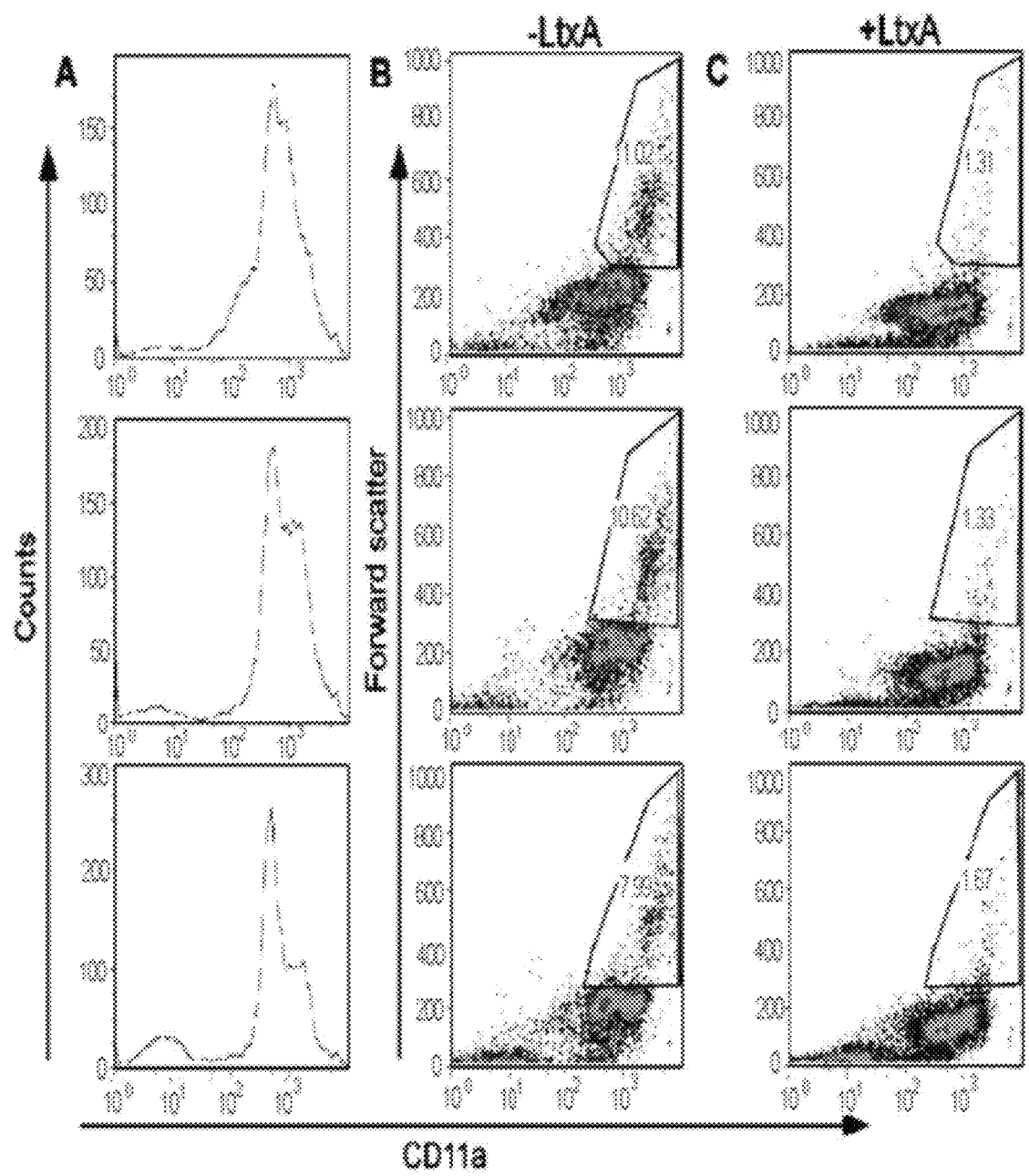
FIG. 2 is a set of diagrams showing flow cytometry results of healthy human PBMCs' staining with anti-LFA-1 antibody and sensitivity to LtxA.
Figure 3:
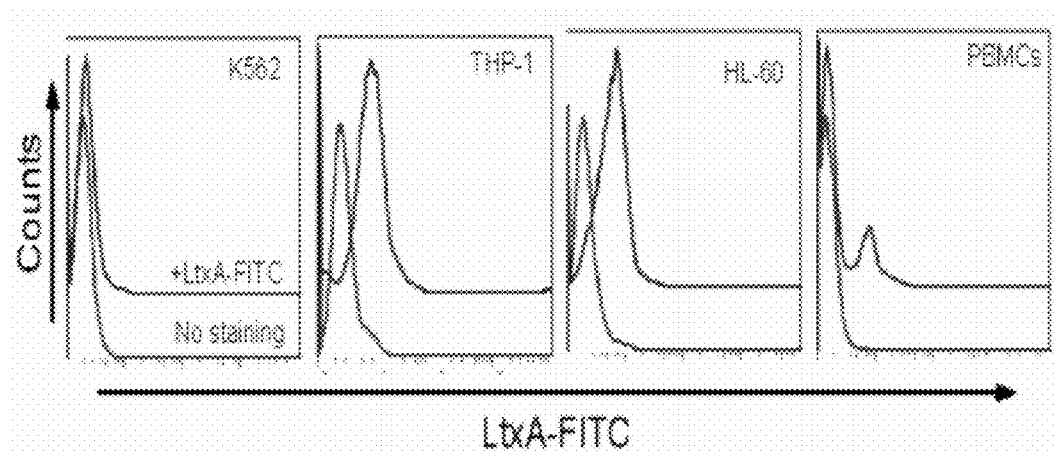
FIG. 3 is a set of diagrams showing flow cytometry results of cells staining with LtxA-FITC.
Figure 4:
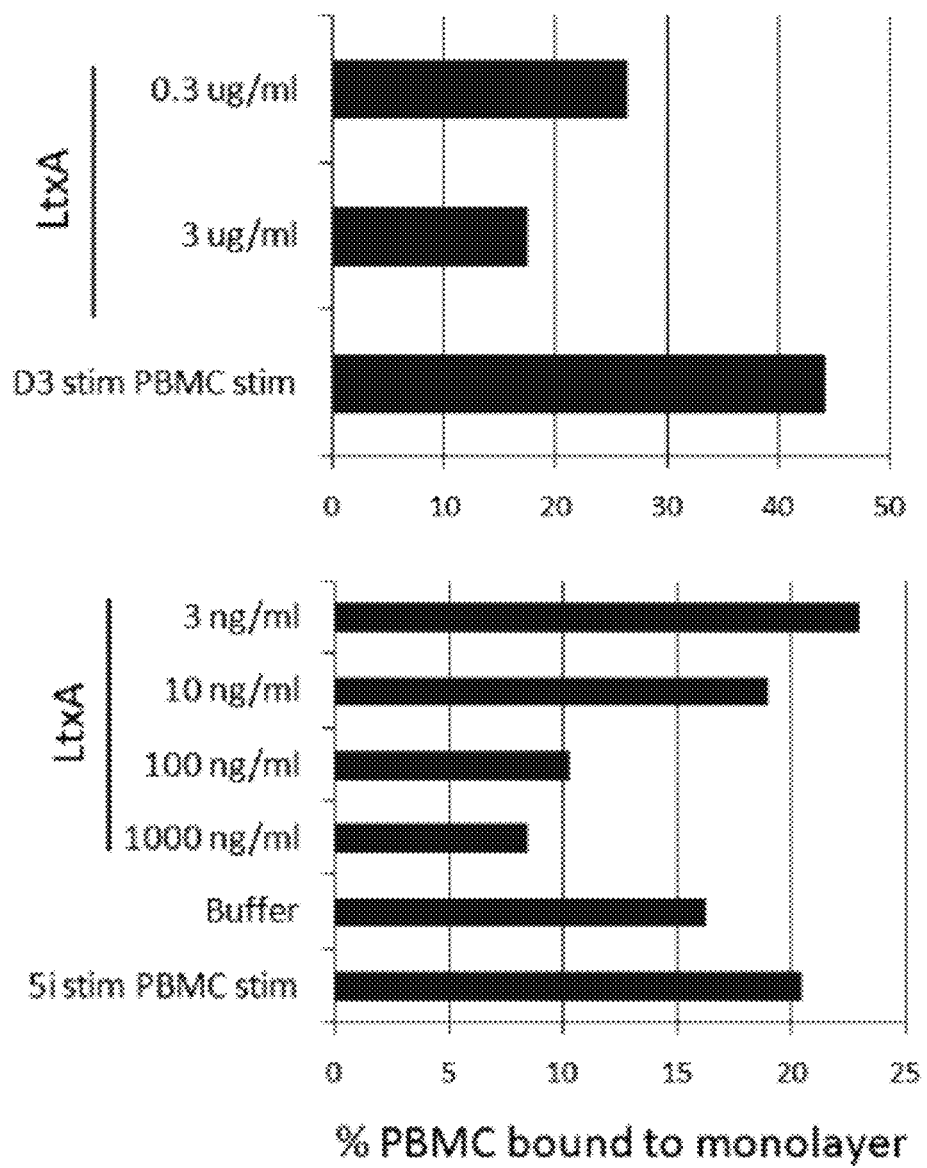
FIG. 4 is a set of diagrams showing binding of activated PBMCs to brain endothelial cells (HBECs).
Figure 5:
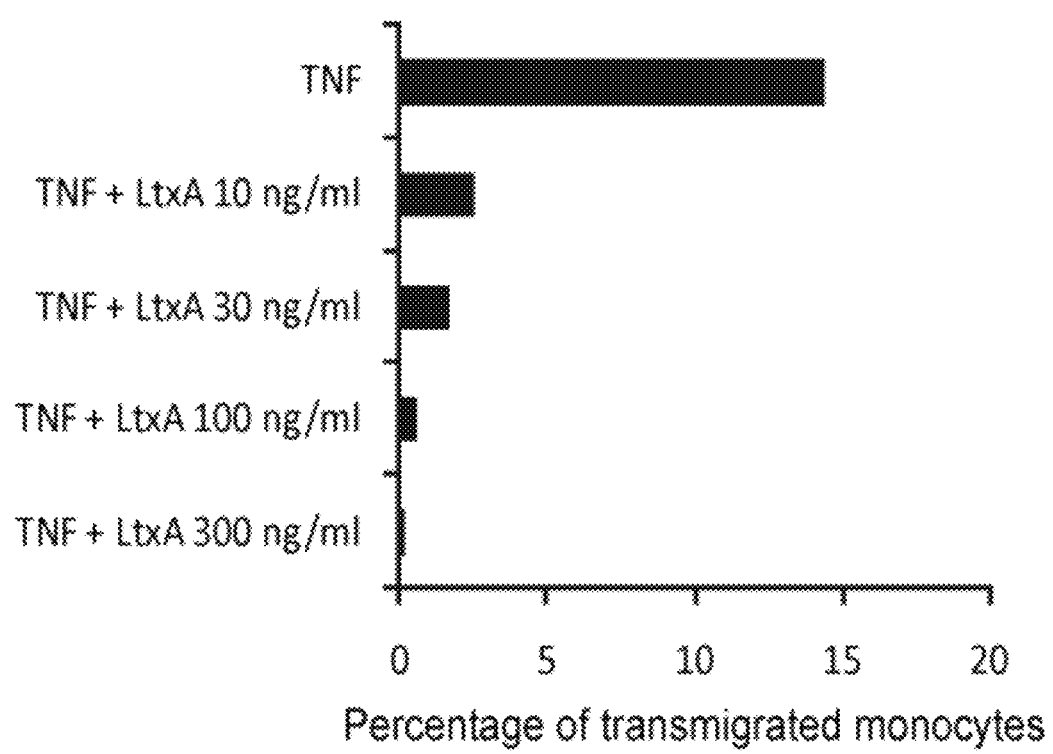
FIG. 5 is a diagram showing migration of WBCs across a brain endothelial cell barrier.

This invention relates to reagents and methods for treating or diagnosing inflammatory disorders, such as autoimmune diseases, as well as to compositions and methods to treat, reduce and prevent HIV infection using LtxA.

Autoimmune Compositions and Methods

There are more than 80 such diseases characterized by the chronic activation of immune cells under non-activating conditions. A major player in the etiology of these conditions is leukocyte function antigen-1 (LFA-1).

LFA-1, a β2-integrin on the surface of white blood cells, is composed of CD11a and CD18 and involved in immune cell migration and signaling. In the absence of infection, circulating WBCs express a "resting state" LFA-1 on their surface. These WBCs play an essential role in immune surveillance, waiting to be called upon by the immune system. During an infection, WBCs need to migrate to the site of insult to destroy the invading pathogens. Extravasation of WBCs into the infected tissue is mediated by signals, such as cytokines, that are released by host cells at the infection site. Inflammatory cytokines cause LFA-1 to assume an active conformation, which results in binding of activated LFA-1 to intercellular adhesion molecule-1 (ICAM-1) on the surface of endothelial cells. The interaction between LFA-1 and ICAM-1 results in migration of WBCs across the endothelial barrier and into the infected tissue. As LFA-1 is involved in the migration of immune cells to various sites of infection, the chronic activation and upregulation of LFA-1 results in the migration of these cells to various tissues of the body, resulting in inflammation and organ damage.

One of the most prevalent autoimmune diseases is psoriasis. This disease, for which there is no cure, affects 2-3% of the population (7-8 million in U.S.; 125 million worldwide). It results from the hyper-activation of immune cells and keratinocytes in the dermis. The immune cells involved in psoriatic lesions have an upregulation and activation of LFA-1. Efalizumab (RAPTIVA), a recombinant monoclonal antibody which binds to the CD11 subunit of LFA-1, was approved for clinical use in patients with this condition but has been withdrawn from the market due to increased risk of viral infection of the central nervous system (progressive multifocal leukoencephalopathy), bacteria sepsis, invasive fungal disease, and other opportunistic infections.

Current treatment for psoriasis includes topical therapy, phototherapy, and systemic administration of steroids and biologics. Many of the therapeutic options are not highly targeted (e.g., steroids, anthralin) however, and exhibit toxic side effects (e.g., biologics, cyclosporine, methotrexate, retinoids). Indeed, the most effective therapies are also considered to have the greatest adverse reactions. Furthermore, over time, psoriasis can become resistant to specific therapies and these treatments are periodically changed to prevent both the development of drug resistance and the occurrence of adverse reactions. This practice is known as treatment rotation.

This invention is based, at least in part, on the unexpected discoveries that LtxA efficiently and specifically targets and kills WBCs that express the activated conformation of LFA-1 on their surface while having little or no toxic effect on other cells or organs in the body. As disclosed in the examples below, LtxA is highly effective in treating psoriasis with minimal toxicity because of its target specificity.

LtxA

LtxA is a ~115 kDa protein produced by the Gram negative bacterium *Aggregatibacter actimomycetemcomitans* (Kachlany, S. C. 2010. *J Dent Res* 89:561-570.). LtxA specifically kills leukocytes of humans and Old World Primates by forming pores in the membrane and causing apoptosis or necrosis (Mangan et al., 1991. *Infect Immun* 59:3267-72.). LtxA binds specifically to LFA-1 and cells that lack LFA-1 are resistant to its toxicity (Kachlany, S. C. et al., 2010. *Leukemia Research* 34:777-85.). For example, LtxA is not active against human red blood cells, human epithelial cells, rat cells, or mouse cells. LtxA also remains active in the presence of human peripheral blood.

Since LtxA is able to identify and kill white blood cells resulting from auto-immune disease, it is an ideal agent for both the detection and treatment of these conditions. For example, blood from a patient can be analyzed using LtxA-FITC staining. A finding of a large percentage of activated WBCs indicates that the patient should undergo LtxA therapy. The effectiveness of the leukotoxin treatments can be monitored by employing LtxA-FITC reagent that initially diagnosed the disease. As the patient responds positively to treatment, the number of WBCs with upregulated activated surface LFA-1 should be seen to decrease. Further, because of LtxA's highly specific targeting ability, few side effects are expected.

LtxA is able to kill many leukemia and lymphoma cell lines and preclinical studies have shown that it may be an effective targeted therapy for treating hematological malignancies. LtxA is expected to be more advantageous than Efalizumab because it displays a significantly greater selective action by only targeting active LFA-1 and thereby mainly destroying activated leukocytes involved in disease. In non-human primates, it was found that a single LtxA treatment depleted leukocyte counts for only 12 hours and high doses administered to mice were found to be non-toxic.

While many LtxA preparations can be used, highly purified LtxA is preferred. Examples include LtxA polypeptide purified from Aggregatibacter actimomycetemcomitans (SEQ ID NO: 1 shown above) and other variants having substantially the same biological activity as that having the sequence of SEQ ID NO: 1. It was discovered that Aggregatibacter actimomycetemcomitans secreted active LtxA into culture supernatants (Kachlany, S. C., et al. 2000. Infect Immun 68:6094-100) and an efficient method for its purification was described in Kachlany, S. C., et at. 2002. *Protein Expr Purif* 25:465-71. This method can therefore be used to prepare isolated or purified LtxA polypeptide. In one example, a purification procedure of the toxin involves:

a. inoculating a single colony of Aggregatibacter actimomycetemcomitans into a fresh broth and growing cultures;
b. adding the growing cultures to fresh broth, adding glass beads and incubating;
c. centrifuging the incubated culture, forming a pellet and a supernatant;
d. filtering the supernatant through a membrane to provided a filtered supernatant;
e. mixing $(NH_4)_2SO_4$ and the filtered supernatant together to form a mixture;
f. centrifuging the mixture to form as mixture pellet;
g. resuspending the mixture pellet in buffer to form a protein resuspension;
h. passing the protein resuspension through a column; and
i. collecting the protein eluting off the column.

See also PCT/US2006/45258 (WO 2007/062150) and US Application 20090075883 (U.S. Ser. No. 12/154,843). The contents of these two documents are incorporated herein by reference.

An "isolated polypeptide" refers to a polypeptide that has been separated from other proteins, lipids, and nucleic acids with which it is naturally associated. The polypeptide can constitutes at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A functional equivalent of LtxA refers to a polypeptide derivative of the LtxA polypeptide, e.g., a protein having one or more point mutations, insertions, deletions, truncations, a fusion protein, or a combination thereof. It retains substantially the activity of the LtxA polypeptide, i.e., the ability to target and kill WBCs that express the activated conformation of LFA-1 on their surface while having little or no toxic effect on other cells or organs in the body. The isolated polypeptide can contain SEQ ID NO: 1 or a functional fragment of SEQ ID NO: 1. In general, the functional equivalent is at least 75% (e.g., any number between 75% and 100%, inclusive, e.g., 70%, 80%, 85%, 90%, 95%, and 99%) identical to SEQ ID NO: 1.

All of naturally occurring LtxA, genetic engineered LtxA, and chemically synthesized LtxA can be used to practice the invention disclosed therein. LtxA obtained by recombinant DNA technology may have the same amino acid sequence as naturally a occurring LtxA (SEQ ID NO: 1) or an functionally equivalent thereof. The term "LtxA" also covers chemically modified LtxA. Examples of chemically modified LtxA include LtxA subjected to conformational change, addition or deletion of a sugar chain, and LtxA to which a compound such as polyethylene glycol has been bound. Once purified and tested by standard methods or according to the method described in the examples below, LtxA can be included in pharmaceutical composition, e.g., a topical composition.

The amino acid composition of the LtxA polypeptide described herein may vary without disrupting the ability of the polypeptide to target and kill WBCs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the ability to improve skin condition to identify mutants that retain the activity as descried below in the examples.

A LtxA polypeptide as described in this invention can be obtained as a naturally occurring polypeptide or a recombinant polypeptide. To prepare a recombinant polypeptide, a nucleic acid encoding it (e.g., SEQ ID NO: 2) can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Compositions

Within the scope of this invention is a composition that contains a suitable carrier and one or more of the active agents described above, e.g., LtxA. The composition can be a pharmaceutical composition that contains a pharmaceutically acceptable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. The term "pharmaceutically acceptable carrier" refers to any of the standard pharmaceutical carriers, such as a phosphate buffered saline solution, water, emulsions, and various types of wetting agents. The compositions also can include stabilizers and preservatives. A pharmaceutically acceptable carrier, after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active agent. Examples of other carriers include colloidal silicon oxide, magnesium stearate, cellulose, and sodium lauryl sulfite.

Pharmaceutical compositions for topical administration according to the present invention can be formulated as solutions, ointments, creams, suspensions, lotions, powders, pastes, gels, sprays, aerosols, or oils. Alternatively, topical formulations can he in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incomptibility, instability, allergic response, and the like. The carrier enables an active agent (such as LtxA) and optional component to be delivered to the skin at an appropriate concentration(s). The carrier can thus act as a diluent, dispersant, solvent, or the like to ensure that the active materials are applied to and distributed evenly over the selected target at an appropriate concentration. The carrier can be solid, semi-solid, or liquid. Preferably, it is in the form of a lotion, a cream, or a gel, in particular one that has a sufficient thickness or yield point to prevent the active materials from sedimenting. The carrier can be inert or possess dermatological benefits of its own. It should also be physically and chemically compatible with the active components described herein, and should not unduly impair stability, efficacy, or other use benefits associated with the composition.

The topical composition may be a cosmetic or dermatologic product in the form known in the art for topical or transdermal applications, including solutions, aerosols, creams, gels, patches, ointment, lotion, or foam.

The cosmetic composition may contain a wide variety of optional components, provided that such optional components are physically and chemically compatible with the essential components described herein. Examples of such components include those described in, e.g., U.S. Pat. No. 7,405,195; Harry's Cosmeticology, 7th Ed., Harry & Wilkinson (Hill Publishers, London 1982); Pharmaceutical Dosage Forms—Disperse Systems; Lieberman, Rieger & Banker, Vols. 1 (1988) & 2 (1989); Marcel Decker,. Inc.; The Chemistry and Manufacture of Cosmetics, 2nd Ed., deNavarre (Van Nostrand 1962-1965); and The Handbook of Cosmetic Science and Technology, 1st Ed. Knowlton & Pearce (Elsevier 1993).

The topical composition is useful for treating inflammatory disorders in the skin, such as psoriasis. In addition, it is useful in regulating or improving skin condition, including regulating visible or tactile wrinkles or discontinuities in skin, e.g., visible or tactile wrinkles or discontinuities in skin texture or color, more especially those associated with skin inflammation, ageing, or other internal factors (e.g., biochemical changes from within the skin) or external factors (e.g., radiation, environmental pollution, wind, heat, low humidity, harsh surfactants, and abrasives).

Treatment Methods

The above-described active agents or a composition containing the agents can be used to treat an inflammatory disorder. Accordingly, the invention also features methods for treating in a subject an inflammatory disorder, e.g., an autoimmune disease. Autoimmune diseases are disorders characterized by the chronic activation of immune cells under non-activating conditions. Examples include psoriasis, inflammatory bowel diseases (e.g., Crohn's disease and ulcerative colitis), rheumatoid arthritis, psoriatic arthritis, multiple sclerosis, lupus, type I diabetes, primary biliary cirrhosis, and transplant.

Among the above-listed diseases, psoriasis is the most prevalent autoimmune disease, affecting 2-3% of the population. Psoriasis is a disease that affects the dermis and results from the hyper-activation of immune cells and keratinocytes. It has been found that immune cells involved in psoriatic lesions have an upregulation of LFA-1 (de Boer et al., *Archives of dermatological research* 1994; 286: 304-311 and McGregor et al., *Journal of the American Academy of Dermatology* 1992: 27: 383-388.) In fact, Efalizumab (RAPTIVA) is a monoclonal antibody therapy that is indicated for the treatment of psoriasis. Thus, LtxA and Efalizumab both target the same cell type.

Crohn's disease and ulcerative colitis are diseases of the GI tract and result from an influx of immune cells into the intestines. Several studies have shown that LFA-1 is upregulated in colonic lymphocytes involved in the pathogenesis of Crohn's disease and ulcerative colitis (Bernstein et al., *Clinical immunology, Orlando, Fla.* 2002; 104: 67-72 and Vainer et al., *The American journal of surgical pathology* 2000; 24: 1115-1124).

Multiple sclerosis (MS) is characterized by the influx of immune cells into the central nervous system. Studies have also shown upregulated expression of LFA-1 on immune cells collected from blood and cerebral spinal fluid from MS patients (Elovaara et al. *Neurology* 1998; 51: 1703-1708; and Elovaara et al., Archives of neurology 2000; 57: 546-551.). As described below in the example section, LtxA can suppress symptoms of MS via interfering with cell adhesion and deplete highly-activated immune cells in the CNS.

Rheumatoid arthritis is a disease affecting the joints and occurs when activated immune cells migrate to the synovium. Immune cells found in synovial fluid from RA patients have enhanced expression of LFA-1 and blocking LFA-1 has proven an effective therapeutic strategy in experimental animal systems (see, e.g., Singh et al., *J Immunol* 2008; 180: 1971-1978). Thus, LtxA would preferentially affect and eliminate the immune cells involved in RA pathogenesis.

Systemic lupus erythematosus or lupus is an autoimmune disease that affects primarily women and for which there is little effective treatment. The disease is characterized by immune complex-mediated tissue injury. Activated immune cells are responsible for the production of immune complexes. These immune cells express LFA-1 at high levels and several studies have shown the critical importance of LFA-1-expressing cells in the development of lupus (see, e.g., Kevil et al., *The American journal of pathology;* 2004; 165: 609-616.). Accordingly, LtxA can be used in treating systemic lupus erythematosus.

Other examples of inflammatory disorders that can be treated with LtxA include asthma, myocardial infarction, stroke, inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), acute respiratory distress syndrome, fulminant hepatitis, hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), and allergic rhinitis. Additional examples also include myasthenia gravis, juvenile onset diabetes, glomerulonephritis, autoimmune throiditis, ankylosing spondylitis, systemic sclerosis, acute and chronic inflammatory diseases (e.g., systemic anaphylaxis or hypersensitivity responses, drug allergies, insect sting allergies, allograft rejection, and graft-versus-host disease), and Sjogren's syndrome.

In addition to the above-listed inflammation-related disorders, LtxA can also be used to treat tuberculosis (TB). Approximately one-third of the world's population infected with the bacterial agent that causes TB, *Mycobacterium tuberculosis*. Upon infection, *M. tuberculosis* enters into a latent state where it lives within macrophages. Inside the macrophage, the bacterium remains hidden from the immune system and is very difficult to eradicate. Indeed, bacterial latency and subsequent reactivation are key components of tuberculosis pathogenesis. Aggressive antibiotic therapy consisting of isoniazid and rifampin is prescribed for 9-12 months. Because of this prolonged course of therapy, compliance is a major concern and few patients complete the full regimen. It was reported that *M. tuberculosis*-infected macrophages have an over-abundance of LFA-1 proteins on their surfaces (DesJardin et al., *Microbiology* 2002; 148: 3161-3171.). This induction of LFA-1 expression occurs upon interaction between the bacterium and macrophage host cell. Thus, *M. tuberculosis*-infected macrophages would also be targets for LtxA and LtxA can be used for depleting latently-infected cells. This action would essentially expose bacteria, thereby eliminating the protection of the host cell and rendering the pathogen susceptible to the immune system and systemic antibiotic therapy.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

A subject to be treated for an inflammatory disorder can be identified by standard diagnosing techniques for the disorder. Optionally, the subject can be examined for the level or percentage of WBCs that bind to LtxA in a test sample obtained from the subject by methods described below. If the binding level or percentage is at or above a threshold value (which can be obtained from a normal subject), the subject is a candidate for treatment with an effective amount of LtxA.

"Treating" or "treatment" refers to administration of a compound or agent to a subject, who has a disorder (such as an inflammatory disorder), with the purpose to cure, alleviate, relieve, remedy, delay the onset of, or ameliorate the disorder, the symptom of the disorder, the disease state secondary to the disorder, or the predisposition toward the disorder. A "therapeutically effective amount" refers to the amount of an agent sufficient to effect beneficial or desired results. A therapeutically effective amount can be administered in one or more administrations, applications or dosages and is not intended to be limited to a particular formulation or administration route.

The agent can be administered in vivo or ex vivo, alone or co-administered in conjunction with other drugs or therapy. As used herein, the term "co-administration" or "co-administered" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, LtxA is administered to a subject. Generally, LtxA is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery.

Diagnostic and Prognostic Methods

As discussed above, LFA-1, present on WBCs of inflammatory disease patients, can act as a marker to detect and monitor the treatment of these afflictions while providing a therapeutic target for pharmaceutical agents. LtxA specifically targets WBCs that express the activated conformation of LFA-1, and therefore can be used in diagnosing diseases meditated by such WBCs.

To that end, this invention also features diagnosis methods. WBCs expressing the activated conformation of LFA-1 can be detected in a subject based on the presence of the binding of LtxA in a test sample from the subject. In other words, the binding of LtxA can be used as markers to indicate the presence or absence of WBCs involved in inflammatory disorders, including autoimmune diseases. Diagnostic and prognostic assays of the invention include methods for assessing the binding level of LtxA with WBCs.

The binding level in a test sample can be evaluated by obtaining a test sample from a test subject and contacting the test sample with LtxA. The "test sample" includes tissues, cells and biological fluids isolated from a subject, as well as tissues, cells and fluids present within a subject. The level of binding of LtxA to WBCs can be measured in a number of ways, including that described in the examples below. In a preferred embodiment, LtxA or its fragments that mediate binding between LtxA and LFA-1 (i.e., probes) are labeled with a detectable agent. The term "labeled" is intended to encompass direct labeling of the probe by physically linking a detectable substance to the probe, as well as indirect labeling of the probe by reactivity with a detectable substance. For example, LtxA (or its fragment) can be indirectly labeled using a second antibody directed against LtxA, wherein the second antibody is coupled to a detectable substance. Examples of detectable substances or labels include radio isotopes (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluoresceing isothiocyanate, rhodamine, phycoerythrin, GFP, or BFP), or luminescent moieties (e.g., QDOT™ nanoparticles by the Quantum Dot Corporation, Palo Alto, Calif.).

LtxA not only binds to, but also kills, WBCs. In the diagnostic or prognostic method, to minimize any potential errors caused by cell death, the binding of LtxA and WBCs can be conducted at low temperatures (e.g., 0-4° C.) and for a short period of time such as 5 to 20 or 30 minutes.

The prognostic assays described herein can be used to determine whether a subject is suitable to be administered with an agent (e.g., a drug) to treat an inflammatory disorder. For example, such assays can be used to determine whether a subject can be administered with a cytotoxic drug or immunesuppressants to treat an autoimmune disorder, including those involved in organ/tissue transplantation.

Thus, also featured in this invention is a method of monitoring a treatment inflammatory disorders (e.g., an autoimmune disorder) in a subject. For this purpose, the binding level between LtxA and WBCs can be determined for test samples from a subject before, during, or after undergoing a treatment. A decrease in the binding level after the treatment indicates that the subject can be further treated by the same treatment. For example, a patient who has received organ or tissue transplantation often faces the problems of organ or tissue rejection. That is, the body has an immune response to an organ or tissue which causes failure of the transplant. To address this problem, organ or tissue transplantation is often accompanied by nonspecific immune suppression therapy to prevent T cell-mediated rejection. However, these immunosuppressants can cause infection, hypertension, cancer, and other undesirable side effects. Therefore, there is a need for monitoring the suppression. To that end, LtxA's biding level can serve as a marker for a proper level or degree of immune suppression. A skilled in the art can adjust the amount of immunosuppressants and length of treatment based on the level of the binding during the course of the treatment.

Information obtained from practice of the above assays is useful in prognostication, identifying progression of, and clinical management of diseases and other deleterious conditions affecting an individual's health status. The information more specifically assists the clinician in designing therapy or other treatment regimes to treat inflammatory disorders, including autoimmune diseases.

HIV Compositions and Methods

HIV infection is characterized by a latent period in which the virus stably integrates into the host genome. In this way, HIV is able to hide from the host immune system and lays dormant for potentially years. Reactivation of the virus can occur and result in AIDS.

HIV preferentially infects memory CD4+ T cells, which over-express the adhesion integrin, leukocyte function antigen-1 (LFA-1). LFA-1 is a β2-integrin on the surface of white blood cells (WBCs). It is composed of CD11a and CD18 and involved in immune cell migration and signaling. In the absence of infection, circulating WBCs express a "resting state" LFA-1 on their surface. LFA-1 and its ICAM-1 ligand play an important role in promoting HIV-1 infectivity and transmission. These molecules are present on the envelope of HIV-1 virions and are integral components of the HIV virological synapse. However, cellular activation is required to convert LFA-1 to the active conformation that has high affinity binding for ICAM-1.

As disclosed herein, it was unexpected that HIV-1 gp120 was sufficient to trigger LFA-1 activation in fully quiescent naïve CD4 T cells in a CD4 and chemokine receptor-dependent manner, and that these CD4 T cells became more susceptible to killing by cytotoxic agents that target activated LFA-1. Accordingly, this invention provides cytotoxic agents that target activated LFA-1 for eliminating HIV-infected cells, thereby treating or controlling HIV infection.

One example of the LFA-1-targeting cytotoxic agents is LtxA or its functional equivalent. Replicating and residing inside macrophages and T-lymphocytes, HIV viruses are difficult to combat using conventional anti-retroviral therapy because the viruses "hide" from the immune system inside host cells. As disclosed herein, LtxA is highly effective in killing HIV-infected cells. For example, virus p24-expressing CD4 T cells in the peripheral blood of HIV-infected subjects were found to have higher levels of surface LFA-1, and LtxA treatment led to significant reduction of the viral DNA burden. These results demonstrate the use of leukotoxin to destroy HIV-1-infected cells independent of the virus variability and deplete the virus reservoir that cannot be eradicated by the conventional therapy.

Once these infected cells are destroyed, the virus would be released and acted upon by the natural host immune defenses. Otherwise, integrated virus-containing T-cells would be killed, thus removing the potential threat of reactivation at a later time. Leukotoxin treatment in this case is different from other therapies in that the therapy is not directed against the virus (which would select for resistant HIV mutants), but rather against the host cell in which the virus resides. That is, by targeting the cells and specifically the invariable cellular adhesion molecule LFA-1, the aforementioned LtxA treatment circumvents the problems of virus variability and drug resistance that conventional therapy faces.

While many LtxA preparations can be used to practice this invention, highly purified LtxA is preferred. Examples include LtxA polypeptide purified from *Aggregatibacter actimomycetemcomitans* (SEQ ID NO: 1 shown above) and other variants having substantially the same biological activity as that having the sequence of SEQ ID NO: 1. It was discovered that *Aggregatibacter actimomycetemcomitans* secreted active LtxA into culture supernatants (Kachlany, S. C., et al. 2000. *Infect Immun* 68:6094-100) and an efficient method for its purification was described in Kachlany, S. C., et al. 2002. *Protein Expr Purif* 25:465-71. This method can therefore be used to prepare isolated or purified LtxA polypeptide. In one example, a purification procedure of the toxin involves: (a) inoculating a single colony of *Aggregatibacter actimomycetemcomitans* into a fresh broth and growing cultures; (b) adding the growing cultures to fresh broth, adding glass beads and incubating; (c) centrifuging the incubated culture, forming a pellet and a supernatant; (d) filtering the supernatant through a membrane to provided a filtered supernatant; (e) mixing $(NH_4)_2SO_4$ and the filtered supernatant together to form a mixture; (f) centrifuging the mixture to form a mixture pellet; (g) resuspending the mixture pellet in buffer to form a protein resuspension; (h) passing the protein resuspension through a column; and (i) collecting the protein eluting off the column. See also PCT/US2006/45258 (WO 2007/062150), US Application 20080318252 (U.S. Ser. No. 12/150,038), and US Application 20090075883 (U.S. Ser. No. 12/154,843). The contents of these patent documents are incorporated herein by reference.

An "isolated polypeptide" refers to a polypeptide that has been separated from other proteins, lipids, and nucleic acids with which it is naturally associated. The polypeptide can constitute at least 10% (i.e., any percentage between 10% and 100% inclusive, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A functional equivalent of LtxA refers to a polypeptide derivative of the LtxA polypeptide, e.g., a protein having one or more point mutations, insertions, deletions, truncations, a fusion protein, or a combination thereof. It retains substantially the activity of the LtxA polypeptide, i.e., the ability to target and kill cells that express the activated conformation of LFA-1 on their surface while having little or no toxic effect on other cells or organs in the body. The isolated polypeptide can contain SEQ ID NO: 1 or a functional fragment of SEQ ID NO: 1. In general, the functional equivalent is at least 75% (e.g., any number between 75% and 100%, inclusive, e.g., 70%, 80%, 85%, 90%, 95%, and 99%) identical to SEQ ID NO: 1.

All of naturally occurring LtxA, genetic engineered LtxA, and chemically synthesized LtxA can be used to practice the invention disclosed therein. LtxA obtained by recombinant DNA technology may have the same amino acid sequence as naturally a occurring LtxA (SEQ ID NO: 1) or an functionally equivalent thereof. The term leukotoxin or LtxA also covers chemically modified leukotoxin or LtxA. Examples of chemically modified LtxA include LtxA subjected to conformational change, addition or deletion of a sugar chain, and LtxA to which a compound such as polyethylene glycol has been bound. Once purified and tested by standard methods or according to the method described in the examples below, LtxA can be included in pharmaceutical composition, e.g., a topical composition.

The amino acid composition of the LtxA polypeptide described herein may vary without disrupting the ability of the polypeptide to target and kill WBCs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the ability to kill LFA-1 positive cells to identify mutants that retain the activity as descried below in the examples.

A LtxA polypeptide as described in this invention can be obtained as a naturally occurring polypeptide or a recombinant polypeptide. In addition to leukotoxin or LtxA, other examples of the aforementioned LFA-1-targeting cytotoxic agents include antibody-based cytotoxic agents. The term "antibody" refers to an immunoglobulin molecule or immunologically active portion thereof, i.e., an antigen-binding portion. Examples include a protein having at least one, and preferably two, heavy (H) chain variable regions ($V_H$), and at least one and preferably two light (L) chain variable regions ($V_L$). The $V_H$ and $V_L$ regions can be further subdivided into regions of hypervariability, termed "complementarity determining regions" ("CDR"), interspersed with regions that are more conserved, termed "framework regions" (FR). As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes.

Antibodies that are specifically binds to activated LFA-1 can be made using methods known in the art. An anti-LFA-1 antibody can be a polyclonal or a monoclonal antibody. Examples of such antibodies include monoclonal antibody MEM-83 as marketed by ABCAM PLC (Cambridge, Mass.) and described in Hogg et al. 1993. *Am Rev Respir Dis,* 148, S55-59, and similar antibodies descried in Porter et al. 2002 *J Immunol,* 168, 6330-6335 (e.g., mAb38 and mAb G25.2).

In one embodiment, the antibody can be recombinantly produced, e.g., produced by phage display or by combinatorial methods. In another ne embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate ( e.g., monkey), camel antibody.

To make antibody based cytotoxic agents, the above-mentioned antibody can be conjugated to a cytotoxic agent with methods known in the art. Examples of cytotoxic agents include radioactive isotopes (e.g., phosphorus-32, copper-67, arsenic-77, rhodium-105, palladium-109, silver-111, tin-121, iodine-125 or 131, holmium-166, lutetium-177, rhenium-186 or 188, iridium-194, gold-199, astatium-211, yttrium-90, samarium-153, or bismuth-212), chemotherapeutic agents, e.g., methotrexate, adriamicin, vinca alkaloids (vincristine, vinblastine, etoposide), doxorubicin, melphalan, mitomycin C, chloramucil, daunorubicin, or other intercalating agents, enzymes and fragments thereof such as nucleolytic enzymes, antibiotics, and toxins such as small molecule toxins or enzymatically active toxins of bacterial (e.g., Diptheria toxin, Pseudomonas endotoxin and exotoxin, Staphylococcal enterotoxin A), fungal (e.g., α-sarcin, restrictocin), plant (e.g., abrin, ricin, modeccin, viscumin, pokeweed anti-viral protein, saporin, gelonin, momoridin, trichosanthin, barley toxin) or animal origin, e.g., cytotoxic RNases, such as extracellular pancreatic RNases; DNase I, including fragments and/or variants thereof.

The above-described active agents target an invariant cellular protein LFA-1. Thus, the activity of the active agents is not affected by the tremendous genetic, biologic, and antigenic variation of HIV-1. Hence, an approach based on these agents to eradicate HIV-infected cells differs from strategies of utilizing toxin-conjugated CD4 or antibodies that target productively infected cells via the virus envelope antigens which are not only highly variable but are also occluded to various degrees in the vast majority of HIV-1 clinical isolates (Kennedy, et al. 2006. *J Leukoc Biol* 80:1175-1182, and Pincus, et al. 2001. *AIDS Res Hum Retroviruses* 19:901-908). The approach disclosed herein is also different from utilizing LFA-1 antagonists that are aimed to reduce the efficiency of virus-cell interaction for suppressing virus infection and transmission.

By destroying virus-infected cells that are left unaffected by the current anti-retroviral therapy (ART), the above-described active agents (e.g., LtxA) can work in synergy with ART to significantly lower or eliminate the overall virus burden in HIV-infected individuals. It was known that ART can successfully reduce viremia to <50 copies/ml, but the virus often still replicates at low levels in infected CD4 T cells and other cell types (Brennan, et al. 2009. *J Virol* 83:8470-8481 and Fischer, et al. 2000. *AIDS Res Hum Retroviruses* 16:1135-1140.). The above-described active agents (e.g., LtxA) can be used to deplete these productively infected cells and eradicate the residual active virus infection. In addition, intermittent transient viremia is frequently detected in well suppressed HIV-infected subjects on ART (Di Mascio et al. 2004. *J Virol* 78:10566-10573; Fischer, et al. 2000. *AIDS Res Hum Retroviruses* 16:1135-1140; and Nettles et al., 2005. *Jama* 293:817-829.) Such viral blips are thought to result from activation of latently-infected cells by antigen recognition or bystanders in a local inflammatory response (Jones et al. 2007. *Acquir Immune Defic Syndr* 45:483-493.). The aforementioned active agents are effective against latent infection as well.

Within the scope of this invention is a composition that contains a suitable carrier and one or more of the active agents described above, e.g., LtxA or an anti-LFA-1 antibody based cytotoxic agent. The composition can be a pharmaceutical composition that contains a pharmaceutically acceptable carrier.

Pharmaceutically effective compositions of this invention may be administered to humans and other animals by a variety of methods that may include continuous or intermittent administration. Examples of methods of administration may include, but are not limited to, oral, rectal, parenteral, intracisternal, intrasternal, intravaginal, intraperitoneal, topical, transdermal, buccal, or as an oral or nasal spray. Accordingly, the pharmaceutically effective compositions may also include pharmaceutically acceptable additives, carriers or excipients. Such pharmaceutical compositions may also include the active ingredients formulated together with one or more non-toxic, pharmaceutically acceptable carriers specially formulated for oral administration in solid or liquid form, for parenteral injection or for rectal administration according to standard methods known in the art.

The term "parenteral" administration refers to modes of administration which include intravenous, intramuscular, intraperitoneal, intracisternal, intrasternal, subcutaneous and intraarticular injection and infusion. Injectable mixtures are known in the art and comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils such as olive oil), injectable organic esters (such as ethyl oleate) and suitable mixtures thereof.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents which delay absorption such as aluminum monostearate and gelatin. Injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

In some cases, to prolong the effect of the drug, it is desirable to slow drug absorption from subcutaneous or intramuscular injection. This may be accomplished by using a liquid suspension of crystalline or amorphous material with poor water solubility. The rate of absorption of the drug then depends upon its rate of dissolution which, in turn, may depend upon crystal size and crystalline form. Alternatively, absorption of a parenterally administered drug form may be delayed by dissolving or suspending the drug in an oil vehicle.

To prepare the pharmaceutical compositions of the present invention, an effective amount of the aforementioned agent(s) can be intimately admixed with a pharmaceutically acceptable carrier according to conventional pharmaceutical compounding techniques to produce a dose. A carrier may take a wide variety of forms depending on the form of preparation desired for administration, e.g., oral or parenteral.

Actual dosage levels of active ingredients in the pharmaceutical compositions of this invention may be varied so as to obtain amounts of the active agents which are effective to achieve the desired therapeutic response for a particular patient, compositions and mode of administration. The selected dosage level will depend upon the activity of the active agents, the route of administration, the severity of the condition being treated and the condition and prior medical history of the patient being treated. However, it is within the skill of the art to start doses of the agents at levels lower than required to achieve the desired therapeutic effect and to gradually increase the dosage until the desired effect is achieved.

Compositions according to the present invention may also be administered in combination with other agents to enhance the biological activity of such agents. Such agents may include any one or more of the standard anti-HIV agents which are known in the art, including, but not limited to, azidothymidine (AZT), dideoxycytidine (ddC), and dideoxyinosine (ddI). Additional agents which have shown anti-HIV effects and may be combined with compositions in accordance to the invention include, for example, raltegravir, maraviroc, bestatin, human chorionic gonadotropin (hCG), levamisole, estrogen, efaviremz, etravirine, indomethacin, emtricitabine, tenofovir disoproxil fumarate, amprenavir, tipranavir, indinavir, ritonavir, darunavir, enfuvirtide, and gramicidin.

Figure 7:
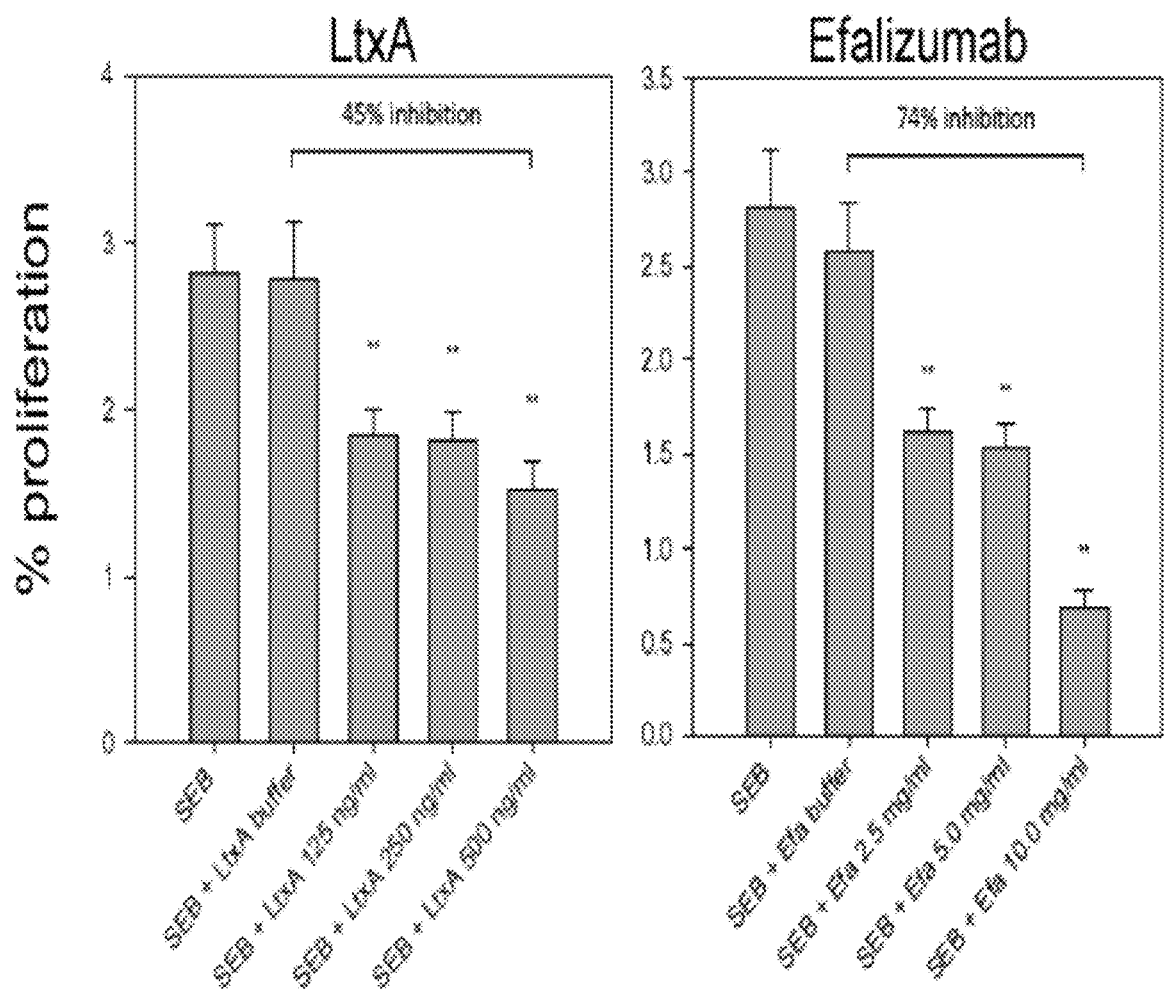
FIG. 7 is a set of diagrams showing effects of LtxA and Efalizumab on proliferation of PBMCs from psoriasis patients.

The above-described active agents or a composition containing the agents can be used to treat or inhibit an HIV infection. Accordingly, the invention also features methods for treating in a subject has, or is suspected of having, an HIV infection.

A subject to be treated can be identified by standard diagnosing techniques for the disorder. "Treating" or "treatment" also refers to administration of a compound or agent to a subject, who has a disorder (such as an HIV infection), with the purpose to cure, alleviate, relieve, remedy, delay the onset of, or ameliorate the disorder, the symptom of the disorder, the disease state secondary to the disorder, or the predisposition toward the disorder. A therapeutically effective amount can be administered in one or more administrations, applications or dosages and is not intended to be limited to a particular formulation or administration route.

The agent can be administered in vivo or ex vivo, alone or co-administered in conjunction with other drugs or therapy. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, the above-described agent. e.g., LtxA, is administered to a subject. Generally, LtxA is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. In an ex vivo approach, a subject's blood can be withdrawn and treated with the above-mentioned agent to remove cells expressing activated LFA-1 before the blood thus-treated is given back to the subject.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of agents available and the different efficiencies of various routes of administration. Variations in these dosage levels can be adjusted using standard empirical routines for optimization as is well understood in the art. Encapsulation of the agent in a suitable delivery vehicle (e.g., polymeric microparticles or implantable devices) may increase the efficiency of delivery.

Unlike microbicides and ART, which require constant adherence, as a prophylaxis LtxA can be administered once or a few times in a short course, soon after virus exposure or during the early phases of the infection, in order to purge a substantial fraction, if not all, of virus-harboring cells from the infected individuals. A significant reduction of viral burden in HIV-infected individuals should have a significant impact in preventing or delaying disease progression of these individuals, as well as reducing virus transmission to the community. LtxA may also be applied as a therapeutic agent, in conjunction with or after successful ART to eradicate most, if not all, virus-infected cells that remain. Hence, the use of LtxA has the potential to shorten, or perhaps eliminate, ART, which is currently considered to be lifelong. A limited course of LtxA treatment will also reduce the potential of eliciting the host immune response that may neutralize this bacterial toxin.

In one example, LtxA may be administered once or a few times in a short course after ART in the acute or chronic phases of the infection. Indeed, three doses of LtxA to leukemic mice were sufficient to eliminate the malignancy and result in long-term disease-free progression (Kachlany, S. C. et al., 2010. *Leukemia Research* 34:777-85). The short-course intermittent administration of LtxA should reduce the risk of severe immunosuppression as reported with the clinical use of Efalizumab, a monoclonal antibody against the CD11a subunit of LFA-1 for treatment of psoriasis Korman et al. 2009. *Arch Dermatol* 145:937-94. The capacity of LtxA to purge a substantial fraction of virus-harboring cells from the infected individuals should have a considerable impact in delaying disease progression and decreasing the duration of ART in these individuals, as well as reducing virus transmission to the community.

The invention now being generally described, it will be more readily understood by reference to the following examples, which are included merely for purposes of illustration of certain aspects and embodiments of the present invention, and are not intended to limit the invention.

EXAMPLE 1

In this example, LtxA's targeting of activated LFA-1 on WBCs was demonstrated in a study using a T-lymphocyte cell line (Jurkat) that expresses a high level of constitutively activated LFA-1 and control isogonic cells that either express the wild type form of the receptor or lack LFA-1 expression entirely. It was found that the T-lymphocytes were ten times more sensitive to LtxA-mediated toxicity than the control cells which were not affected.

Malignant human monocyte cell line, THP-1, and peripheral blood mononuclear cells (PBMCs) PBMCs from four healthy adults were also treated with LtxA at different concentrations for 24 hours. Cell viability was then determined by measurement of cellular ATP. The results are shown in FIG. 1B. Untreated samples represent a relative viability of 1.0. The curve for PBMCs represents the average of the four human PBMC samples performed in quadruplicate. The vertical bars represent standard deviation. Results shown are representative of biological duplicates. As shown in FIG. 1B, LtxA had little effect on normal, resting human WBCs by examining its effect on normal PBMCs from healthy donors. The majority of cells were found to be resistant to LtxA and a drop in viability was only observed at very high drug concentrations. PBMCs prepared from healthy adults were also stained with anti-LFA-1 (CD11a) antibodies and analyzed by flow cytometry. Shown in FIG. 2 are results of cell size (forward scatter) vs. CD11a expression after 24-hour treatment with a control ("-LtxA") and LtxA ("LtxA"). As shown in the figures, only the activated cells with high levels of LFA-1 were affected by LtxA.

To determine whether LtxA can detect cells that had activated LFA-1 on their surface, purified LtxA was covalently labeled with a fluorescent substituent, fluorescein isothiocyanate (FITC). This allowed the LtxA to be detected and quantified by fluorescence spectroscopy when used in cell binding experiments. Laboratory studies showed that the LtxA-FITC retained full targeting and biological activity indicating that the FITC modification did not adversely affect toxin structure. Test cells were mixed with LtxA-FITC for 30 minutes at 0° C. (on ice) and the resulting conjugates were analyzed by flow cytometry.

The test cells included K562 cells (which do not express LFA-1 and are unaffected by LtxA), THP-1 cells, HL-60 cells, and PBMCs (from a healthy donor). As shown in FIG. 3, LtxA-FITC did not kill the test cells due to the low temperatures and brief time period used. Further observations determined that K562 cells (which lack CD11a and CD18) did not bind the leukotoxin-FITC, indicating that LFA-1 is required for cell staining. In contrast, LtxA-FITC strongly attached itself to THP-1 cells and with slightly less intensity to HL-60 cells. Similar experiments were carried out with PBMCs, which possess minimal levels of activated surface LEA-1. As expected, it was found that only a small subset of the PBMCs were stained. These results demonstrate that LtxA binds to specific WBCs and that LtxA targets only cells with activated surface LFA-1.

EXAMPLE 2

It was known that the initial steps leading to inflammation include the binding of activated PBMCs to endothelial cells and migration across the endothelial barrier. Strategies to treat inflammatory disorders therefore include depletion of those WBCs that are involved in pathogenesis and interruption of their binding and migration into the affected tissue. In this example, assays were carried out to determine if LtxA could block binding of activated PBMCs to human brain endothelial cells (HBECs) to model the initial steps leading to inflammation.

More specifically, D3 pr 5i HBECs were grown to monolayer on collagen or gelatin and then stimulated with TNF. Calcein-labeled PBMCs activated with PMA were then added to the monolayer and incubated for 2 hours. Unbound cells were washed and the percent PBMC binding was calculated by measuring fluorescence. It was found that LtxA was able to prevent binding of activated PBMCs to the endothelial cells in a dose-dependent manner (FIG. 4). Greater than 50% blocking was observed at higher doses of LtxA. Because these PBMCs were from a healthy individual, complete blocking was not observed since most of the cells were normal and not affected by LtxA. Cytotoxicity assays showed that only approximately 10-20% of the cells stained with propidium iodide after two hours thereby indicating that many of the cells that were blocked by LtxA were not killed. Thus, the above results demonstrate that LtxA has the ability to selectively deplete and block activated PBMCs from binding to endothelial cells.

In addition, in an in vitro model for multiple sclerosis (MS), it was found that LtxA blocked the migration of monocytes across a HBEC layer (FIG. 5). This model represents migration of WBCs into the CNS, which occurs in MS. These results suggest that LtxA can be used in treating MS via its ability to selectively deplete and/or block monocytes from entering into the CNS.

EXAMPLE 3

In this example, assays were carried out to compare the effects of LtxA and anti-LFA-1 mAb Efalizumab on T-cells. More specifically, $5\times10^5$ Jurkat cells/ml were treated with serial dilutions of LtxA Efalizumab for 72 hours before the proliferation of the cells were examined using the CELLTITER GLO kit from PROMEGA. It was found that LtxA decreased proliferation of the cells in a dose-dependent manner (FIG. 6). The inhibition of proliferation increased over time with an $IC_{50}$ value of 250 ng/ml after 72 hours. Efalizumab also decreased proliferation of the cells in a dose-dependent manner; but the time of stimulation did not seem to augment this effect (FIG. 6). The $IC_{50}$ value for Efalizumab was 5 mg/ml at all times. Thus, the effective dose of LtxA is approximately 20,000 times lower than that of Efalizumab.

Assays were also carried out to examine the efficacy of LtxA and Efalizumab on activated PBMCs from psoriasis patients. Briefly, PBMCs were isolated from ten donors with severe plaque psoriasis (three females and seven males, age 29-63 (48±13)). PBMCs were isolated from blood samples by centrifugation over a lymphoprep density gradient and immediately frozen in liquid nitrogen until used. The cells were then activated using Staphylococcal enterotoxin B (SEB) at a final concentration of 1 µg/ml and treated with dilutions of LtxA or Efalizumab. It was found that LtxA inhibited proliferation of the activated PBMCs from psoriasis patients and the effective doses were at least 5000 times lower than those of Efalizumab (FIG. 7).

EXAMPLE 4

In this example, assays were carried out to evaluate the effect of LtxA and Efalizumab in alleviating psoriasis in vivo in a psoriasis xenograft transplantation model. As mentioned above, LFA-1 is a heterodimer consisting of CD11a (αL) and CD18 (β2) integrin subunits. It binds to intercellular adhesion molecule 1 (ICAM-1) present on antigen-presenting cells (APCs) and functions as an adhesion molecule. Binding between LFA-1 and ICAM-1 results in induction of T-cell activation, but also allows anchoring of these cells to the endothelium which is followed by extravasation leading to recruitment of T-cells to the site of inflammation.

Methods

Patient Material:

Two patients with plaques-type psoriasis were identified and keratome skin biopsies from lesional skin were obtained. The patient's psoriasis was un-treated for at least 1 month prior to the time of skin removal.

Xenograft Transplantation Protocol:

Keratome skin biopsies were cut into smaller pieces before transplantation on the back of anesthetized SCID mice (female, 6-8 week of age, M&B Taconic, Denmark). After a healing period of approximately 10 days, the animals were divided into separate treatment groups. A total of 24 mice were entered into the study. Animals were allocated to two consecutive study series, each representing skin grafts from one individual psoriasis patient (total of 2 patients, 12 mice for each series). Each series was subdivided into 4 groups. One group in each series served as untreated control whereas the other groups were allocated to treatment with LtxA, efalizumab, or LtxA vehicle. The allocation scheme was as follows:

| Group | Mice pr group per series | Treatment | Total mice per treatment |
| --- | --- | --- | --- |
| 1 | 2 | untreated | 4 |
| 2 | 4 | Efalizumab | 8 |
| 3 | 4 | LtxA | 8 |
| 4 | 2 | LtxA vehicle | 4 |

LtxA (0.5 mg/kg), efalizumab (6 mg/kg), and LtxA vehicle (Tris buffer/NaCl) was administered once daily by i.p. injection for 3 weeks. These dosages were chosen as it was demonstrated that 2 mg/kg LtxA had a non-toxic therapeutic effect when it was administered in a mouse leukemia xenograft model (Kachlany, S. C. et al., *Leukemia Research* 2010; 34:777-85.). Similarly, administration of 6 mg/kg efalizumab (i.p. daily) or 10 mg/kg anti-ICAM-1 (i.p. every second day) to mice in the psoriasis xenograft transplantation model demonstrated as therapeutic effect (Zeigler M et. al., *Lab Invest* 2001; 81:1253-61 and Boehncke W H et. al., *Br J Dermatol* 2005; 153:758-66).

During treatment, human psoriatic skin grafts were clinically assessed twice weekly and given a semi-quantitative clinical psoriasis score according to the clinical signs: scaliness, induration, and erythema. The parameters were scored using the three-point scale: 0=complete lack of cutaneous involvement; 1=slight involvement; 2=moderate involvement; 3=severe involvement. On this scale from 0 to 3, a maximal score of 3 represents severe scale, induration, and erythema of the psoriatic xenografts.

After 3 weeks and after the final clinical assessment, the animals were killed and 4-mm size punch biopsies were taken centrally from each human psoriatic skin graft. The biopsy samples were paraffin embedded and stained with haematoxylin/eosin (HE). On five HE stained sections the following parameters were assessed: 1) epidermal thickness, 2) parakeratosis, 3) psoriasis pattern, 4) angiogenesis, 5) lymphocytes, and 6) stratum granulosum. Epidermal thickness was measured as the distance from stratum corneum to the deepest part of the rete pegs. Parakeratosis, psoriasis pattern, angiogenesis and lymphocytes were evaluated and given scores in the range 0-4 where 0 denotes no psoriasis and 4 denotes full fledge psoriasis. Stratum granulosum was evaluated in the range 0-4 where 0 denotes full fledge psoriasis and 4 no psoriasis.

Statistic Analysis:

Results are shown as mean ±SEM. The non-parametric Mann Whitney test was used to test for differences between treatment groups in semiquantitative clinical psoriasis scores, parakeratosis scores, psoriasis pattern scores, angiogenesis scores, lymphocyte scores, and stratum granulosum scores. Students t-test was used to test for no differences between treatment groups for epidermal thickness. Observations made for different mice were assumed to be independent of each other. All tests were two-sided and p values<0.05 were considered significant.

Results

Control Treatment (Untreated Versus LtxA Vehicle):

No differences between the vehicle and the untreated groups were found in the semi-quantitative clinical psoriasis, the parakeratosis, the psoriasis pattern, the angiogenesis, the lymphocyte, the stratum granulosum scores, and the epidermal thickness measures for both patients. Therefore these two groups are pooled in the following and named negative control group.

Also, it was found that the mice treated with LtxA did not show any physiological changes during the study period, and their bodyweight increased throughout the study similarly to the negative control treated mice.

Semiquantitative Clinical Psoriasis Score:

Semi-quantitative clinical psoriasis scores provide a superficial evaluation of the graft where the histological scores show a more in depth status. Reduction in epidermal thickness is considered the final endpoint when evaluating the treatment effect.

Figure 8:
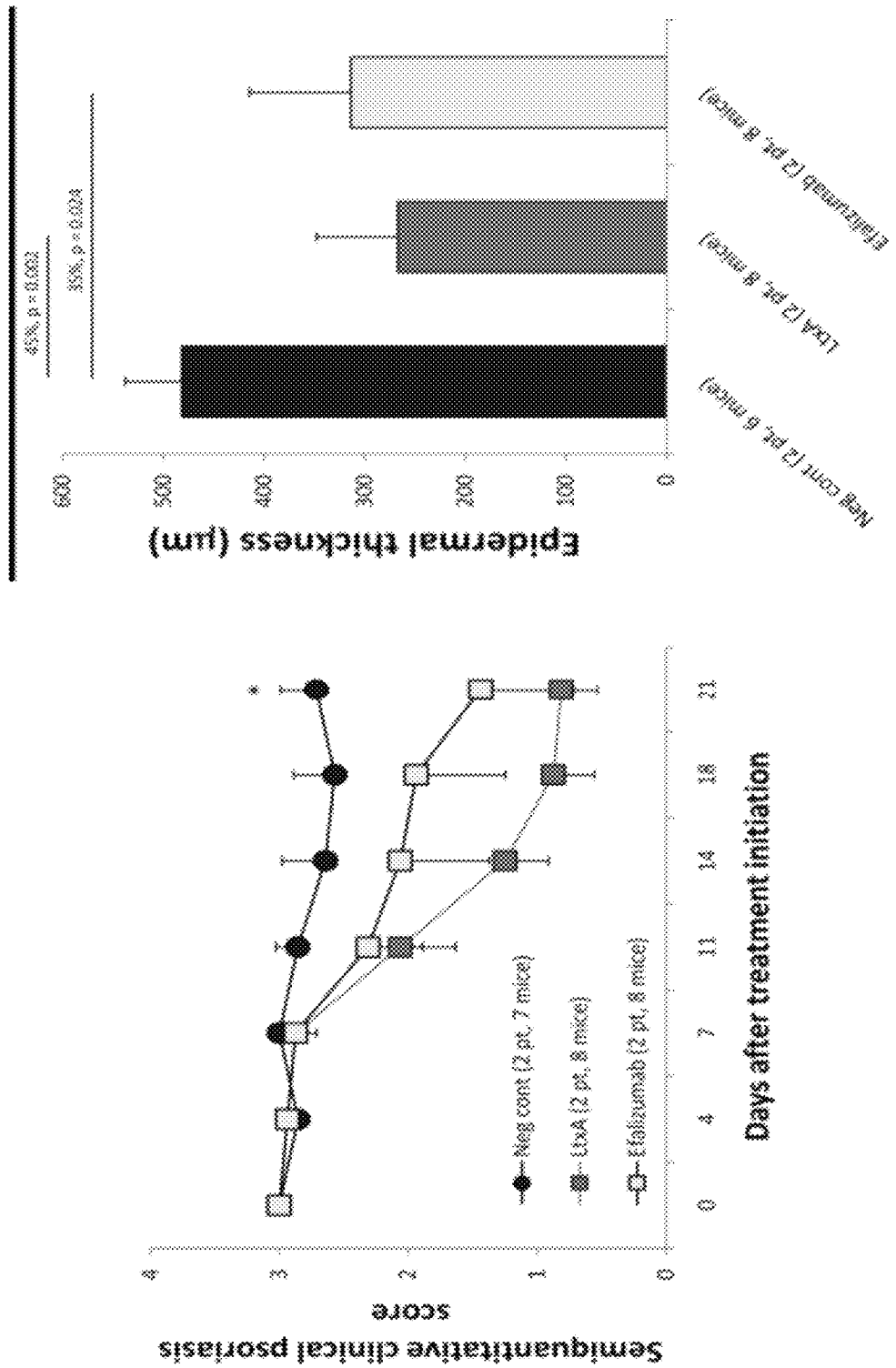
FIG. 8 is a set of diagrams showing effects of LtxA and Efalizumab on semiquantitative clinical psoriasis score and epidermal thickness in psoriasis xenograft transplantation models.

Semiquantitative clinical psoriasis scores were obtained twice weekly throughout the study. As shown in FIG. 8, LtxA significantly decreased the semiquantitative clinical psoriasis score (p<0.001) by 3 weeks treatment. Efalizumab also decreased the semiquantitative clinical psoriasis score (p=0.094) by 3 weeks treatment, however not to a significant degree.

Epidermal Thickness:

After 3 weeks treatment, the mice were killed and biopsies taken from the human psoriatic skin graft. Epidermal thickness was measured on HE stained paraffin embedded sections. It was found that LtxA (p=0.002) and efalizumab (p=0.024) significantly decreased the epidermal thickness. See FIG. 8.

Psoriasis Pattern Scores:

Psoriasis pattern scores give an overall assessment of the psoriatic phenotype observed in the HE stained sections and sums up the results of the epidermal thickness measure, the parakeratosis, the angiogenesis, the lymphocyte, and the stratum granulosum scores. As shown in FIG. 9, LtxA significantly decreased the psoriasis pattern score (p=0.029) by 3 weeks treatment. Efalizumab also decreased the psoriasis pattern score (p=0.059) by 3 weeks treatment, however not to a significant degree.

Parakeratosis Scores:

The parakeratosis scores provide an assessment of the degree of parakeratosis observed in epidermis. Due to the increased turnover and decreased differentiation of keratinocytes in psoriatic skin, parakeratosis (presence of nucleus in desquamated cells) is often present in psoriatic skin. In this study, it was found that LtxA (p=0.282) and efalizumab (p=0.059) decreased the parakeratosis score by 3 weeks treatment, however not to a significant degree. See FIG. 9.

Figure 10:
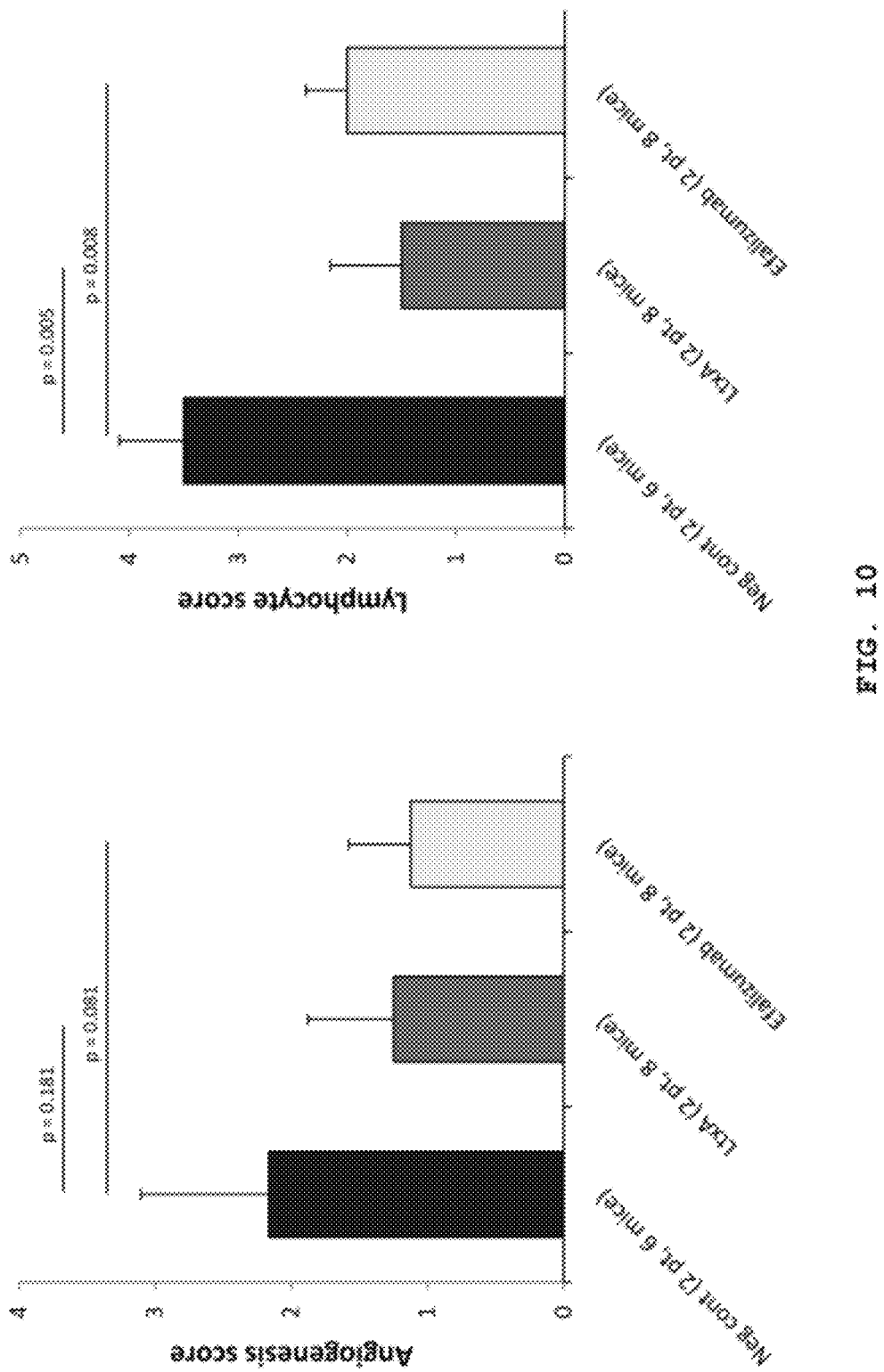
FIG. 10 is a set of diagrams showing effects of LtxA and Efalizumab on angiogenesis scores and lymphocyte scores in the psoriasis xenograft transplantation models.

Angiogenesis Scores:

Angiogenesis scores provide an assessment of the degree of vascularization observed in the dermal compartment. Dermis of psoriatic skin is highly vascularized as compared to the dermis of healthy skin. In this study, it was found that LtxA (p=0.181) and efalizumab (p=0.081) decreased the angiogenesis score 3 weeks treatment, however not to a significant degree See FIG. 10.

Lymphocyte Scores:

Lymphocyte scores provide an assessment of the degree of lymphocytic infiltrate present both in the dermal and the epidermal compartment. Psoriatic skin is characterized by an increased infiltrate of lymphocytes compared to healthy skin. In this study, it was found that LtxA (p=0.005) and efalizumab (p=0.008) both significantly decreased the lymphocyte score by 3 weeks treatment. See FIG. 10.

Figure 11:
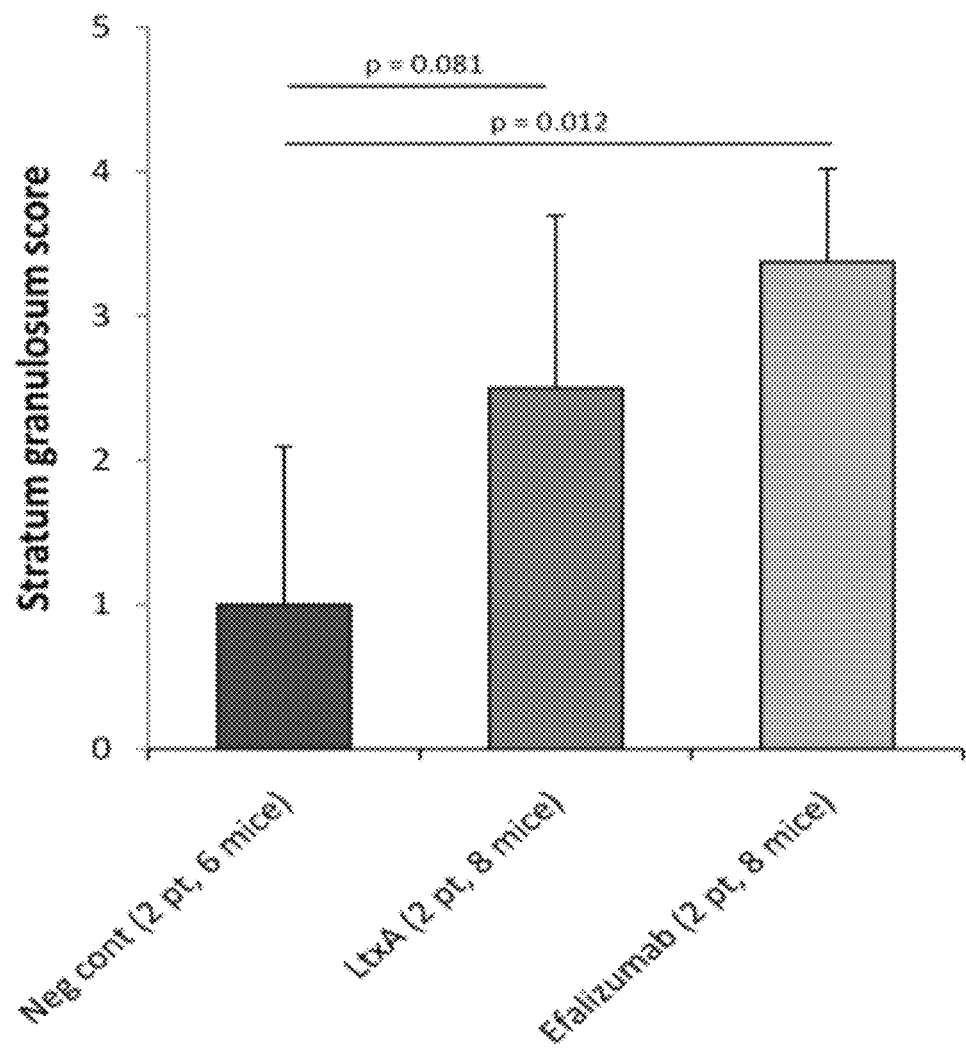
FIG. 11 is as diagram showing effects of LtxA and Efalizumab on stratum granulosum scores in the psoriasis xenograft transplantation models.

Stratum Granulosum Scores:

Stratum granulosum scores provide an assessment of the degree of stratum granulosum presence in the epidermis. Due to the increased turnover and decreased differentiation of keratinocytes in psoriatic skin, this cell layer is typically diminished or lost in psoriatic skin. In this study, it was found that LtxA decreased the stratum granulosum score (p=0.081) by 3 weeks treatment, however not to a significant degree. Efalizumab significantly decreased the stratum granulosum score (p=0.012) by 3 weeks treatment. See FIG. 11.

In sum, the above results demonstrated that the three-week treatment with LtxA significantly decreased the semi-quantitative clinical psoriasis score, the epidermal thickness, psoriasis pattern, and the lymphocyte scores. Efalizumab significantly decreased the epidermal thickness and the lymphocyte scores. Also, this study demonstrated that LtxA significantly alleviated the psoriatic phenotype in the grafted skin from both patients. Efalizumab significantly alleviated the epidermal thickness but not the clinical phenotype of psoriasis. Thus, the results suggest that LtxA is more effective than Efalizumab in treating psoriasis.

EXAMPLE 5

In this example, general materials and methods for carry out various assays are disclosed regarding LtxA and HIV.

Cells:

PBMCs from healthy donors were isolated from leukopacs (New York Blood Center), whereas PBMCs from HIV-infected subjects were from whole blood. The use of human specimens for this study was approved by an institutional review board. After Ficoll-Paque Plus centrifugation, PBMCs were used directly in the experiments or were first enriched for CD4 T cells using a negative-selection magnetic bead kit (MILTENYL BIOTECH or INVITROGEN) as described in Vasiliver-shamis et al. 2009. *J Virol* 83:11341-11355.

Leukotoxin (LtxA):

LtxA was purified from culture supernatants of *A. actinomycetemcomitans* strain NJ4500 as described in Diaz R., et al. 2006. Microb Pathog 40:48-55 and Kachlany, S. C., et al. 2002. *Protein Expr Purif* 25:465-71. Protein was lyophilized in sterile vials and stored at −80° C. Samples were reconstituted in sterile distilled water and filtered through a 0.22 µm filter prior to use. When prepared in this manner, LtxA was stable for at least 6 months.

Planar Bilayer Assay and Microscopy:

Planar bilayers were prepared from liposomes containing 12.5% $Ni^{2+}$-chelating DOGS-NTA (1,2-dioleoyl-sn-glycero-3-[N(5-amino-1-carboxypentyl)iminodiacetic acid] succinyl and glycosylphosphatidylinositol (GPI)-anchored Cy5-labeled mouse ICAM-1 (density of 200-250 molecules/$\mu m^2$) as described in Vasiliver-Shamis et al. 2009. *J Virol* 83:11341-11355 and Vasiliver-shamis et al. 2008. *J Virol* 82:9445-9457. $His_6$ gp120 of HIV-1 DH12 used to reconstitute the bilayers was produced from recombinant vaccinia virus (Cho, M. W., et al. 2001. J Virol 75:2224-2234), labeled with ALEXA FLUOR 488 (INVITROGEN), and applied onto the bilayers at a concentration that resulted in gp120 density of 200 to 250 molecules/$\mu m^2$. After the flow cell containing the bilayers was warmed to 37° C., cells were injected and images collected for 1 hr on a wide-field fluorescence microscope. To test the effects of anti-gp120 mAbs, bilayers were first treated for 20 min with 20 µg/ml of each mAb (EH21, 2219, and 654). The cells were also suspended in a buffer containing 20 µg/ml of the mAb before injection to the bilayers.

Multicolor fluorescence microscopy was performed on an automated microscope with an Orca-ER cooled charge-couple-devise (CCD) camera or electron multiplier CCD camera (HAMAMATSU). The hardware on the microscope was controlled using SCANALYTICS IP-LAB software on a DELL personal computer. Image processing and analyses were performed with IP LAB and METAMORPH software.

Flow Cytometric Analysis:

Surface and intracellular staining of PBMCs was done as described in Kaur, et al. 2007. *Virology* 369:214-225. Fluorescence-conjugated antibodies to CD3 (APC-Cy7) and CD8 (APC) were used to gate CD4 T cell population (CD3+ CD8−) studied, and FITC-conjugated anti-p24 monoclonal antibody (KC57; COULTER) was used to detect CD4 T cells with active HIV replication. LFA-1 expression was measured with PE-conjugated anti-CD11a mAb (BD PHARMINGEN). Data analyses were done with the FLOWJO software (TREE STAR).

Cell Viability Assay:

CD4 T cells ($1 \times 10^5$/well) were added to microtiter wells pre-coated with wild type, mutant, or no gp120, or with soluble gp120, and then treated with LtxA at designated concentrations. For control, cells activated with anti-CD3/anti-CD28 on microtiter wells were also treated with LtxA. After 20 hrs, cellular viability after LtxA treatment was determined using the CELLTITER-GLO luminescent cell viability assay (PROMEGA). Plates were read in PERKIN ELMER VICTOR 3 Multilabel Counter in the luminescence mode.

Real-time PCR:

Cells were lysed by incubation with a lysis buffer (5 mM Tris [pH 8.3], 0.45% TRITON X-100, 0.45% TWEEN 20) and proteinase K (20 mg/ml) for 1 hr at 60° C. and then for 15 min at 95° C. to inactivate proteinase K. Cell lysate (2 µl each) was then used in a 20 µl reaction on the APPLIED BIOSYSTEMS 7900HT FAST REAL-TIME PCR System with 1× SYBR Green SUPERMIX (SYBR Green I Dye, AMPLITAQ GOLD® DNA Polymerase, dNTPs with dUTP, passive reference dye, and optimized buffer components) (APPLIED BIOSYSTEMS) and the specific primers (5 picomoles each). For measuring gag, a 115-bp fragment in the gag region was amplified using the primers SK38 (5'-ATAATCCACCTATC-CCAGTAGGAGAAAT-3', SEQ ID NO: 3) and SK39 (5'-TTTGGTCCTTGTCTTATGTCCAGAATTGC-3', SEQ ID NO: 4) (INVITROGEN) under the following reaction condition: 95° C. for 10 min (initial denaturation) and 40 cycles of 95° C. for 15 sec (denaturation) and 60° C. for 1 min (primer annealing and extension). For β-actin, a 217 bp fragment was amplified using primers 5'-CTCCATCCTGGCCTCGCTGT-3' and 5'-CACCTTCACCGTTCCAGTTT-3' (SEQ ID NOs: 5 and 6) in the following reaction condition: 95° C. for 10 min (initial denaturation) and 40 cycles of 95° C. for 30 sec (denaturation), 55° C. for 30 sec (primer annealing), 60° C. for 1 min (primer extension). PCR products were quantified based on the standard curve in each experiment. The 8E5 LAV cells, each of which contains 1 copy of HIV provirus and 2 copies of β-actin gene, were used to generate the standard curves.

EXAMPLE 6

Figure 12:
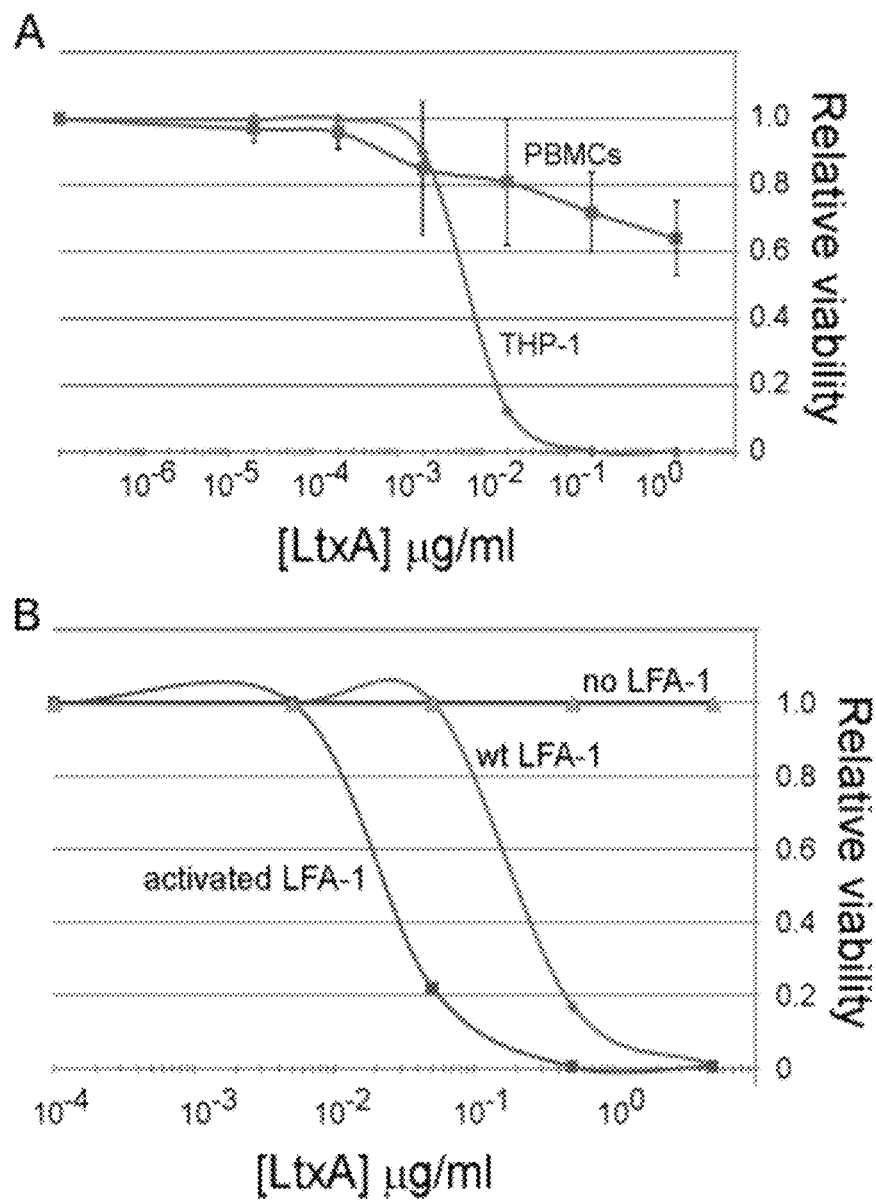
FIGS. 12A and 12B are diagrams showing sensitivity to LtxA-mediated cytotoxicity by THP-1, as malignant human monocyte cell line, and PBMCs from four healthy adults (12A), and by Jurkat-derived T-cells expressing wild type LFA-1, activated LFA-1, or no LFA-1 (12B) with results shown as representative of biological duplicates and vertical bars representing standard deviation.

In this example the specificity of LtxA for activated PMBCs was examined. More specifically, malignant human monocyte cell line, THP-1, and PBMCs from four healthy adults were treated with LtxA at different concentrations for 24 hours. Cell viability was determined by measurement of cellular ATP. The results are shown in FIG. 12A, where untreated samples represent a relative viability of 1.0. The curve for PBMCs represents the average of the four human PBMC samples performed in quadruplicate. As shown in the figure, the cells were generally resistant to killing by LtxA compared to the sensitive leukemia cell line, THP-1 (FIG. 12A).

One hypothesis why some cells are more sensitive to LtxA than others is that LtxA recognizes the activated form of LFA-1 better than LFA-1 in the resting state. To test this, an assay was carried out using Jurkat T-cell line that expresses a high level of constitutively active LFA-1 (J-$\beta_{2.7}$/LFA-1Δ). As controls, isogenic cell lines that either express the wild type form of LFA-1 (J-$\beta_{2.7}$/LFA-1 wt ) or lack LFA-1 expression completely (J-$\beta_{2.7}$/mock) were used. It was found that cells with activated LFA-1 were ten times more sensitive to LtxA-mediated toxicity than cells with resting state LFA-1 and LFA-1-deficient cells were not affected by the toxin (FIG. 12B). Thus, LtxA is more toxic towards WBCs expressing activated form of LFA-1, which are the same type of cells that are preferentially infected by HIV.

Figure 13:
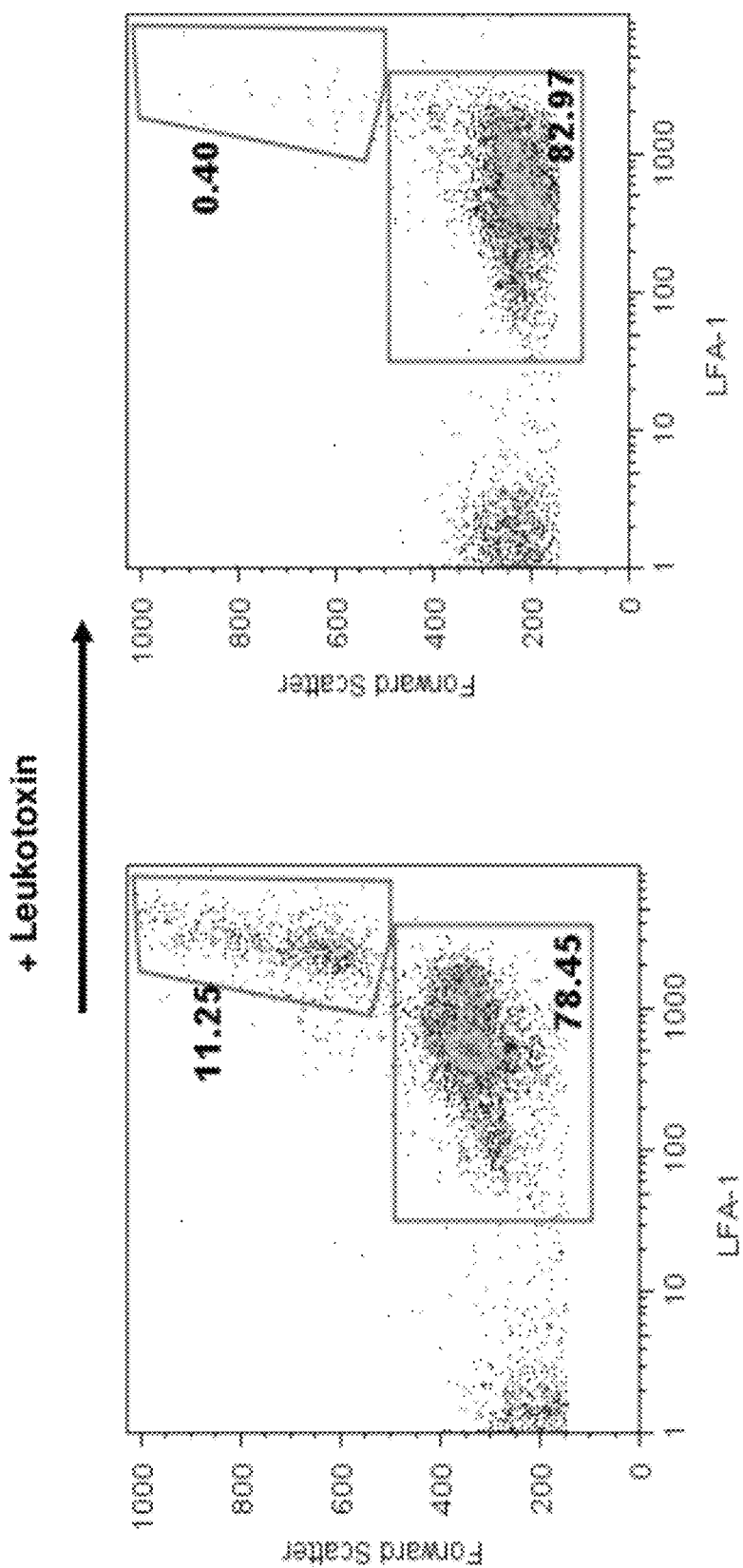
FIG. 13 is a set of flow cytometry histograms showing that LtxA treatment depleted LFA-1$^{hi+}$ cells from PBMCs of an HIV uninfected donor.

The data presented above using the Jurkat cell lines demonstrates that LtxA prefers the activated form of LFA-1 as a target. Furthermore, based on results showing that only a small fraction of healthy PBMCs are affected by LtxA, it is possible that the killed cells represent the small fraction of activated cells in the population. To test this hypothesis, assays were carried out to determine if LtxA retained this specificity for activated LFA-1 in a sample of PBMCs from healthy individuals. After treatment of PBMCs with LtxA, cells were stained for CD3, CD4, and LFA-1, fixed, and analyzed by flow cytometry. It was found that approximately 11% of the CD3+ T lymphocyte population expressed high levels of LFA-1 while 78% expressed low levels (the remaining did not express LFA-1) prior to treatment with LtxA (FIG. 13). Following LtxA treatment, the high LFA-1-expressing cells were almost completely eliminated (a decrease to 0.4%) while the lymphocytes expressing low-levels of LFA-1 (or not expressing LFA-1) were essentially unaffected. The cell population consisted of 96% $CD3^+$ $CD4^+$ T-cells. These results show that LtxA is able to selectively kill activated $CD4^+$ T-lymphocytes in a mixture of PBMCs, suggesting that newly HIV-exposed or infected T-cells would be desired targets for LtxA.

EXAMPLE 7

Figure 14:
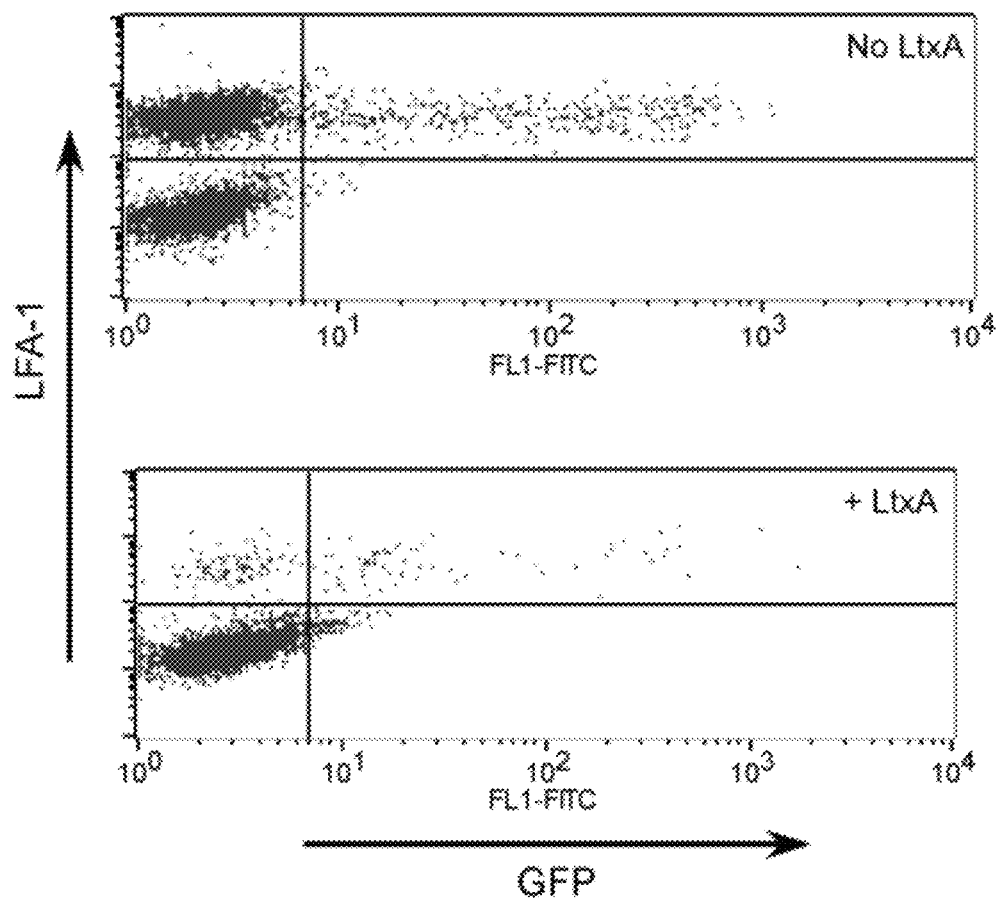
FIG. 14 is a set of flow cytometry histograms showing depletion of LFA-1$^{hi+}$ HIV$^+$ T-cells by LtxA.

In this example, assays were carried out to show effects of LtxA in HIV-infected T-cells. To determine if LtxA could target LFA-$1^+$ T-cells that were infected with HIV, HIV-GFP was used to infect T-cells with either high levels of LFA-1 or not expressing LFA-1. The samples were then treated with LtxA to examine the population that was depleted. Briefly, T-cells bearing LFA-1 and HIV-GFP were mixed with T cells bearing no LFA-1 and then treated with LtxA. The flow cytometry data show that LtxA was able to deplete LFA-$1^+$ cells infected with HIV, but did not affect the population of LFA-$1^-$ cells with no virus (FIG. 14). Thus, the results demonstrate LtxA has the capacity to specifically target LFA-$1^+$ cells that harbor HIV.

Figure 15:
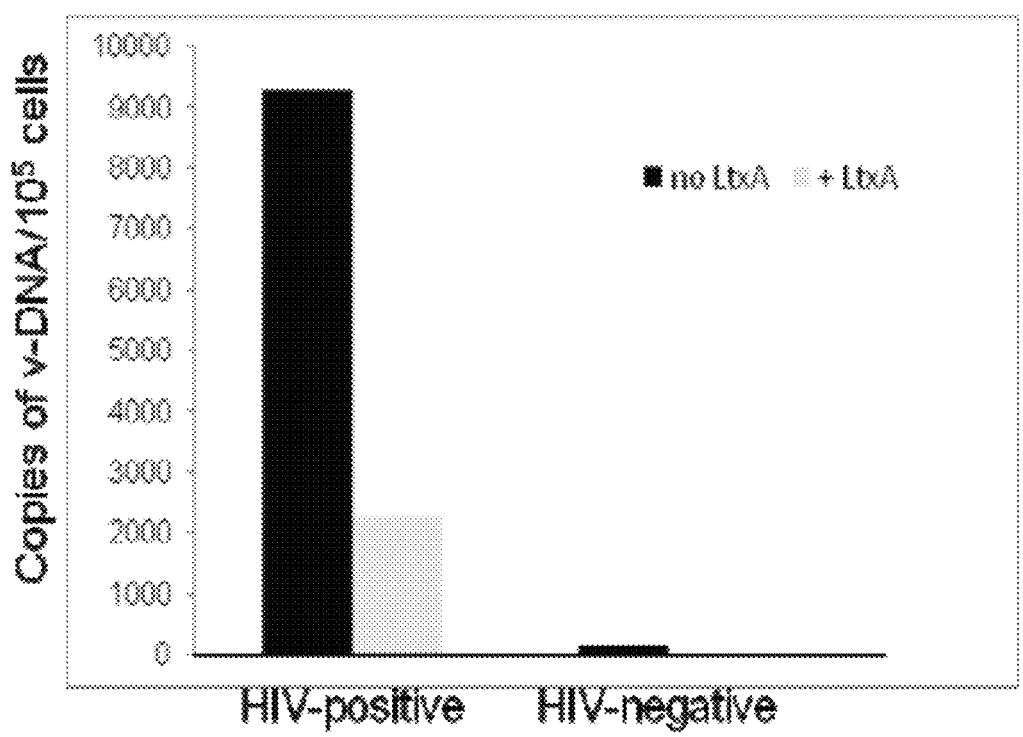
FIG. 15 is a diagram showing qRT-PCR detection of intracellular HIV DNA.

Assays were also carried out to show effects of LtxA on HIV-PBMCs naturally infected with HIV-1 from an HIV-positive patient with a high viral load. Specifically, PBMCs from an HIV-positive individual were treated with LtxA for 24 hours and then intracellular viral DNA remaining was measured by PCR. Viral DNA (not RNA) which identifies intracellular virus (including latent infection) was assayed. An HIV-negative individual was included as a control. It was found that a significant drop in viral DNA occurred after a 24-hour treatment of LtxA (FIG. 15). Thus, the results demonstrate that LtxA is able to deplete latently-infected cells from an HIV-positive patient.

EXAMPLE 8

In this example, assays were carried out to show that the interaction of CD4 T cells with HIV-1 gp120 on bilayers triggers LFA-1 activation and supramolecular re-organization.

Briefly, resting naïve CD4 T cells were obtained ex vivo from the peripheral blood of healthy HIV-seronegative donors. The interaction of the cells with gp120 and ICAM-1 was analyzed on glass-supported planar lipid bilayers. The bilayers served as an experimental model mimicking the virion surface or the infected cell surface (Vasiliver-Shamis, et at. 2009. *J. Virol* 83:11341-11355.). To discern changes in cellular morphology and molecular organization, the bilayers were loaded with ALEXA FLUOR 488-labeled gp120 and Cy5-labeled ICAM-1. For comparison, bilayers were also prepared with Cy5-labeled ICAM-1 alone. After the cells were added onto the bilayers, live images were acquired for up to 1 hr using multicolor fluorescence microscopy.

Naïve peripheral CD4 T cells express LFA-1 in the inactive states with low affinity for ICAM-1. Therefore, these cells rarely form contact with bilayers containing ICAM-1 alone and if they do, the contact is transient.

Figure 20:
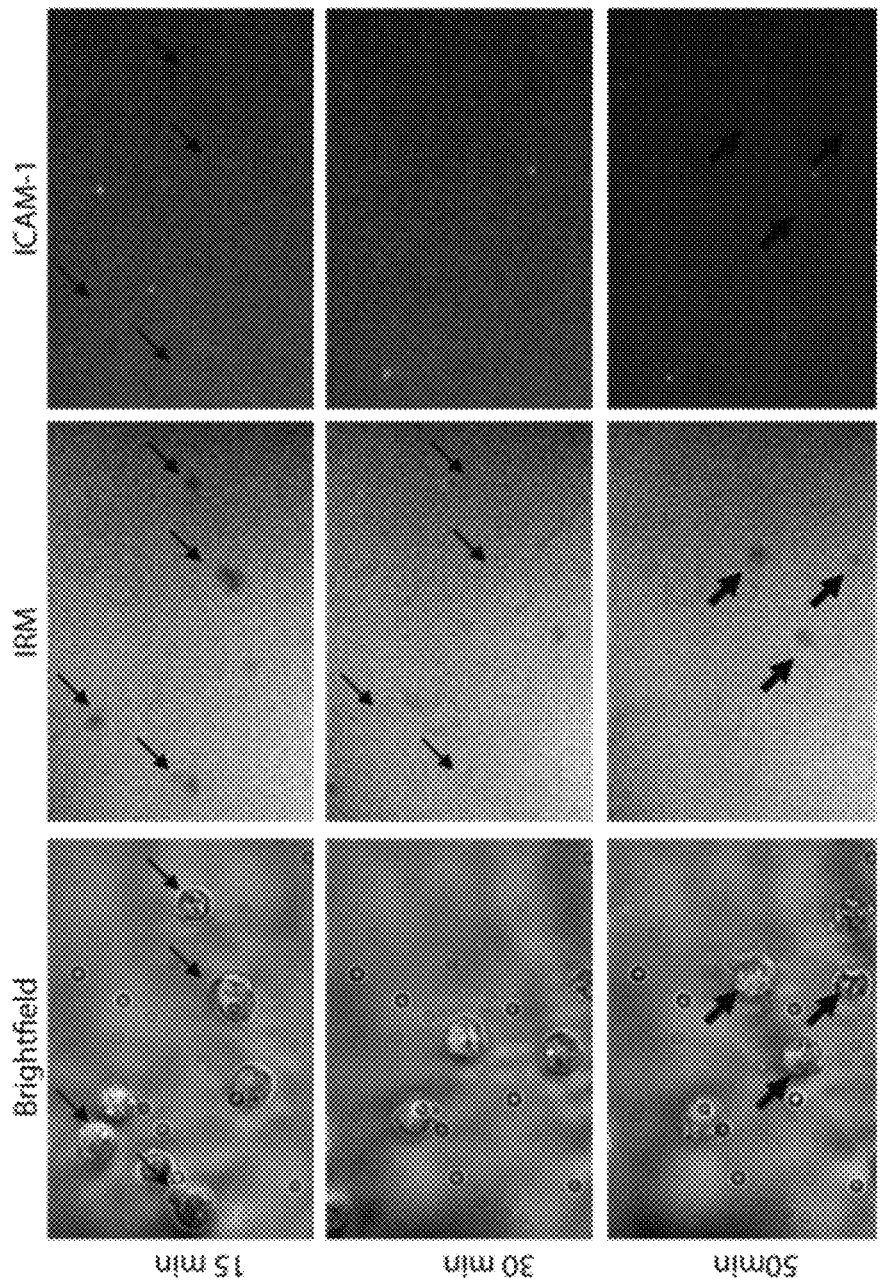
FIG. 20 is a set of photographs showing transient interaction between naïve CD4 T cells and ICAM-1 bilayers, where the same representative field is shown at the indicated time points; black arrows show the cells that interacted transiently with the bilayers at 15, 30, and 50 min.

As shown in FIG. 20, naïve CD4 T cells did not form stable interaction with the ICAM-1 bilayer. The naïve CD4 T cells were injected onto a bilayer containing only ICAM-1 and monitored over one hour for the presence of cells (FIG. 20, bright-field panels), contact with the bilayer (interference reflection microscopy (IRM) panels) and contact with ICAM-1 (ICAM-1 panel). The same representative field is shown at the indicated time points. Thin black arrows show the cells that interacted transiently with the bilayers at 15 min but had no ICAM-1 accumulation and migrated by 30 min. Three new cells interacting with the bilayer at 50 min were also observed and indicated by thick white arrows; again these cells made no ICAM-1 contact.

Figure 16A:
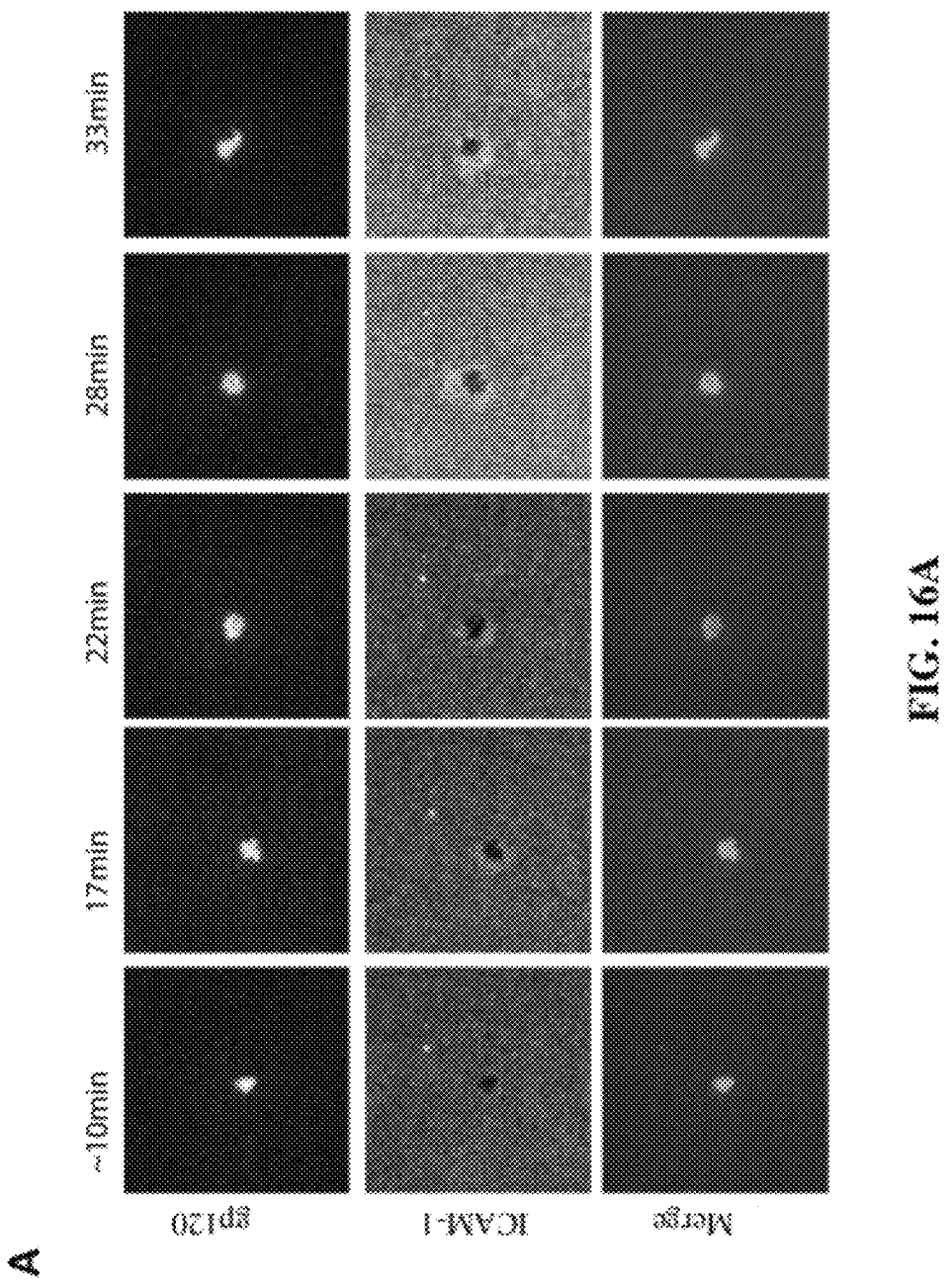

However, when these cells were introduced onto bilayers containing gp120 and ICAM-1, cells established gp120 contacts within the first 5-10 min and 10 min later started forming ICAM-1 contact (FIG. 16A). About 40% of the cells established stable LFA-1-ICAM-1-mediated adhesion (FIG. 16B). In addition, supramolecular rearrangements of both gp120 and ICAM-1 were observed: gp120 accumulated into a central cluster and ICAM-1 assembled into a ring, which is either symmetrical (for 20% of the cells; FIG. 16B, top) or asymmetrical (for another 20%; FIG. 16B, bottom), around the central gp120 cluster.

Figure 6:
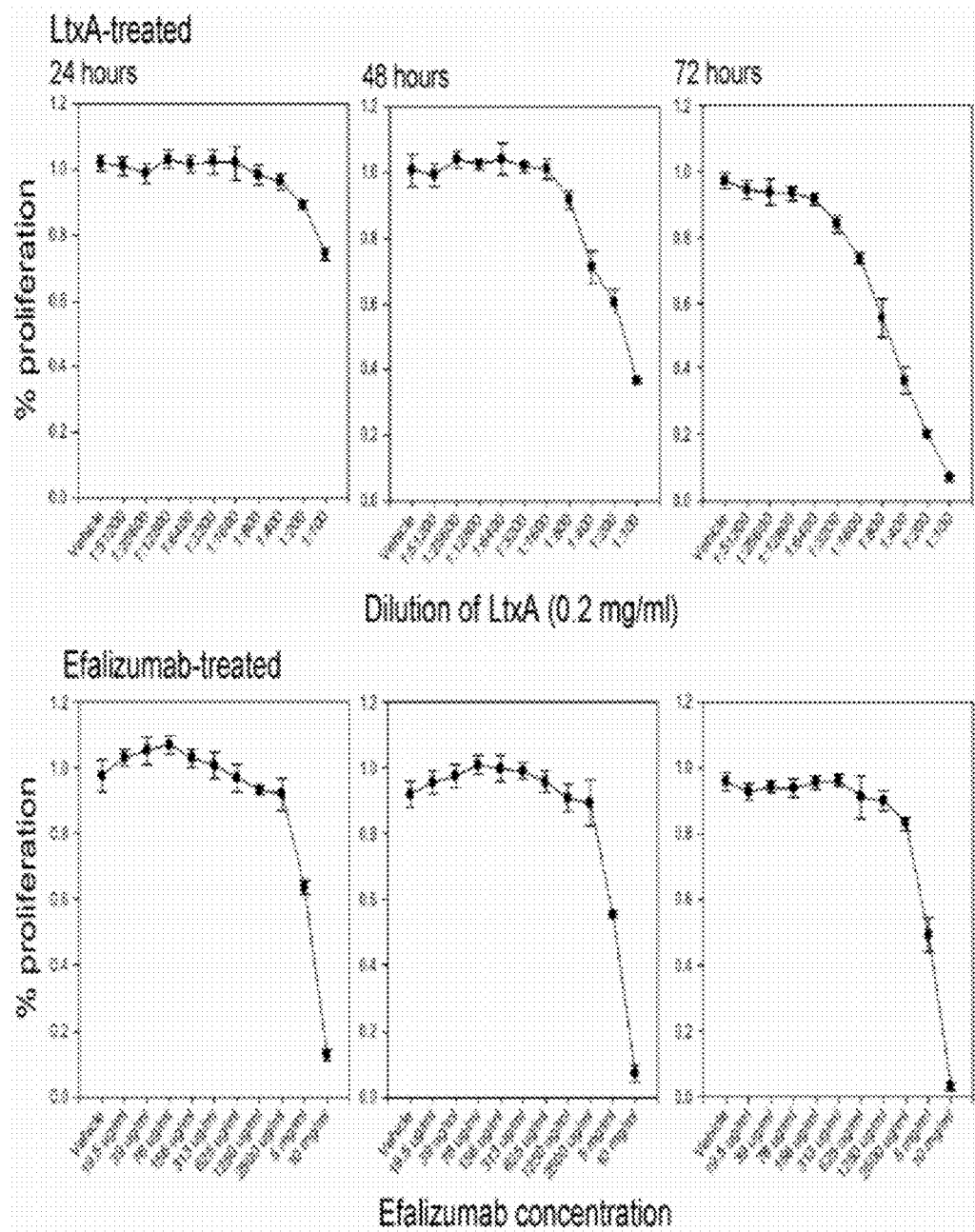
FIG. 6 is a set diagrams showing effects of LtxA and Efalizumab on proliferation of T-cells.

Once formed, this morphology was maintained for the duration of the experiment (1 hr). The LFA-1-ICAM-1 interaction and rearrangement were triggered specifically by gp120 binding to its receptors on the T cell surface, since pre-treatment with mAbs (20 µg/ml) to the CD4-binding site (654) substantially reduced not only the numbers of cells forming gp120 contact (FIG. 16C, left graph), but also ICAM-1 contact (FIG. 6C, right graph). A mAb (20 µg/ml) against the V3 loop (2219), which is involved in binding the chemokine receptor, also decreased both gp120 and ICAM-1 contacts, while a control mAb to the N-terminus of gp120 (EH21) which does not participate in CD4 or the chemokine receptor binding had no effect.

The above results demonstrate that gp120 binding to CD4 and the co-receptor on fully quiescent CD4 T cells triggers LFA-1 activation and supramolecular organization.

EXAMPLE 9

As shown in EXAMPLE 8 above, LFA-1 activation is triggered by gp120 upon binding to CD4 T cells. It is surmised that these cells should become highly susceptible to LtxA, a bacterial leukotoxin that is known to preferentially kill leukocytes with high levels of the activated form of LFA-1. In this example, assays were carried out to show that CD4 T cells exposed to surface-bound gp120 are more susceptible to killing by LtxA.

Specifically, resting CD4 T cells from healthy uninfected donors were incubated on tissue culture wells coated with or without gp120 ((10 µg/ml)) and then treated with different concentrations of LtxA. After 20 hrs, cell viability was determined by measurement of cellular ATP. A mutant gp120 protein lacking the ability to bind CD4 and the chemokine receptors (CD4bs– V3–) was tested as a control.

Figure 17:
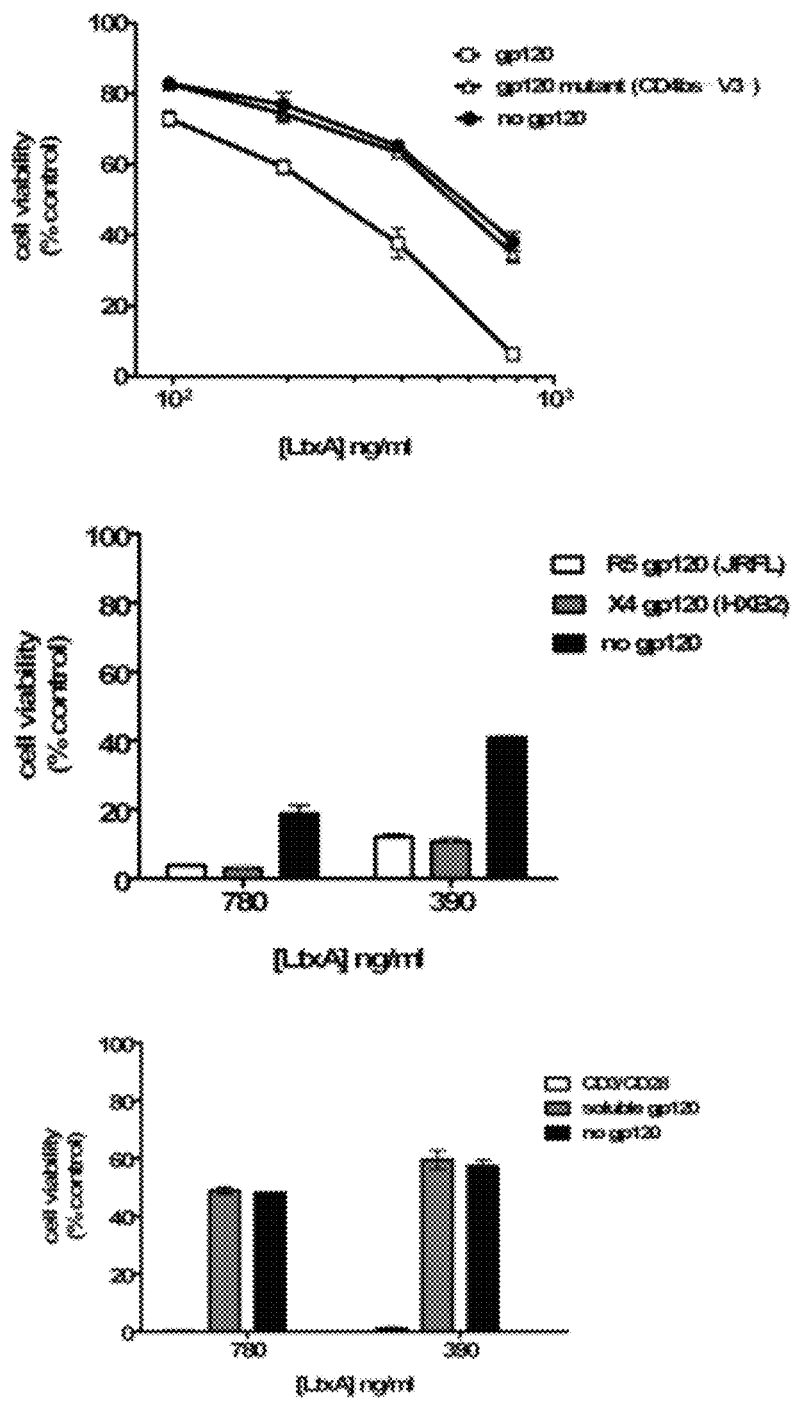
FIG. 17 is a set of diagrams showing effects on cell viability of the interaction of quiescent CD4 T cells with surface-bound wild type gp120, a mutant gp120 lacking CD4-binding site and V3, R5 gp120 (JRFL), X4 gp120 (HXB2), anti-CD3/anti-CD28, and soluble gp120, where data from one of two or more representative experiments are shown and the averages and standard deviation from duplicate wells are presented.

As shown in FIG. 17, CD4 T cells interacting with gp120 on the wells were more susceptible to LtxA than the cells incubated with the mutated gp120 or no gp120. The increased killing was apparent at different concentrations of LtxA. The 50% effective dose (ED50) of LtxA against gp120-treated CD4 T cells was 367 ng/ml, while the ED50 of LtxA against untreated cells and mutant gp120-treated cells were 437 and 440 ng/ml, respectively.

Furthermore, R5 gp120 (JRFL) and X4 gp120 (HXB2) was tested for comparison. CD4 T cells were treated with soluble gp120 or anti-CD3/anti-CD28 coated on microtiter wells prior to addition of LtxA. After incubation with LtxA for 20 hrs, the cell viability was measured based on cellular ATP. It was found that both R5 gp120 and X4 gp120 mediated enhanced susceptibility to LtxA (FIG. 17). However, this activity was induced only when the CD4 T cells interacted with gp120 bound on the well surface; soluble gp120 did not have the same effect (FIG. 17), indicating that gp120-mediated crosslinking of CD4 and/or the chemokine receptor is essential for LFA-1 activation that renders the CD4 T cells more susceptible to killing by LFA-1-specific LtxA. For comparison, CD4 T cells activated by surface-bound anti-CD3 and anti-CD28 antibodies were also treated with LtxA, and nearly 100% of these cells were killed by LtxA at the concentrations tested (390 and 780 ng/ml) (FIG. 17). This contrasts to only ~50% of untreated CD4 T cells susceptible to LtxA at the same concentrations, confirming strong preference of LtxA for LFA-1 on activated I cells.

The above results demonstrate that gp120 binding to quiescent CD4 T cells renders the cells more susceptible to LtxA due to LFA-1 activation as a result of CD4 and/or the chemokine receptor crosslinking, but the gp120-induced activity is not as potent as that triggered by TCR engagement.

EXAMPLE 10

In this example, assays were carried out to show that viral p24-producing CD4 T cells in the peripheral blood of HIV-infected subjects display higher levels of surface LFA-1 expression.

Figure 18:
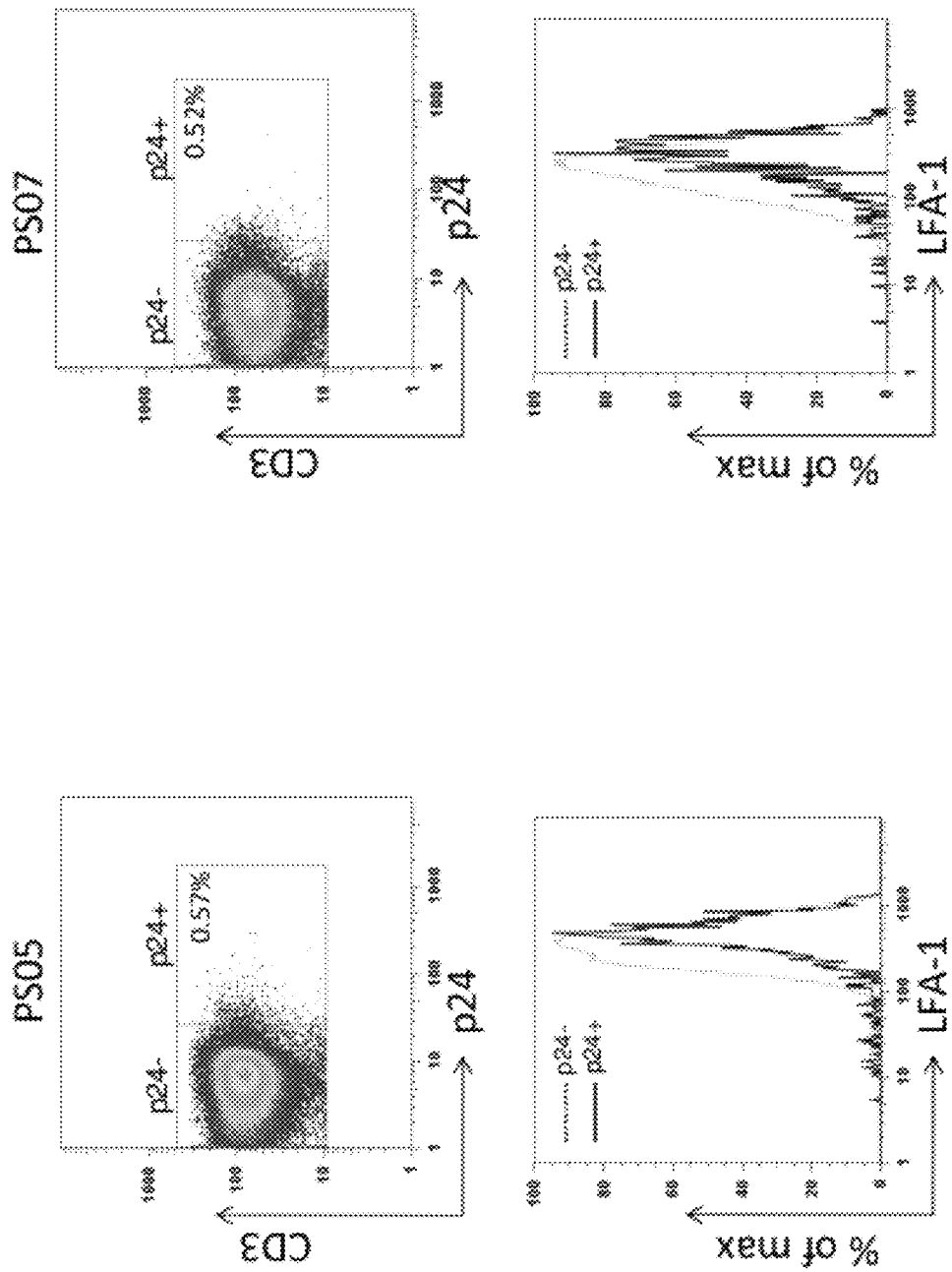
FIG. 18 is a set of diagrams showing that CD4 T cells bearing HIV p24 antigen express higher levels of surface LFA-1 expression.

To evaluate LFA-1 expression on HIV-infected CD4 T cells in the peripheral blood, assay was conducted to analyze ex vivo PBMCs from two viremic untreated HIV-infected subjects (PS05 and PS07) who were asymptomatic and had CD4 count of >450. The PBMCs were stained with mAbs for surface expression of CD3, CD8, and LFA-1, as well as for intracellular p24 antigen after permeabilization. The cells were subjected to flow cytometric analyses, and the data analyzed by the FLOWJO software. The results are shown in FIG. 18, where the dot plots (top panels) show that 0.57% and 0.52% of p24+ CD3+ CD8– T cells were detected in subjects PS05 and PS07, respectively. The p24+ gating is based on the p24 staining of HIV-seronegative PBMCs tested in parallel in each assay. See FIG. 21A, which shows the background p24 staining of CD4 T cells (CD3+ CD8–) from a HIV-seronegative donor, NG05. This gating was used to determine positive p24 staining in the CD4 T cells of HIV-seropositive subjects.

When the LFA-1 expression of p24+ and p24– cells was compared, higher mean fluorescence intensity (mfi) levels were detected on the p24+ cell population than on the p24– cell population from the same subjects, indicative of the activated state of HIV-infected CD4 T cells producing viral p24 antigens in the peripheral blood (FIG. 18). The histograms (bottom) compared LFA-1 expression on p24+ and p24– CD4 T cells; the mfi for p24+ and p24– CD4 T cells are 462 and 376 for PS05, and 311 and 228 for PS07. The higher LFA-1 expression levels were specific as no increase in CD3 expression was observed on p24+ cells as compared to p24– cells (FIG. 21B). Similarly, as shown in FIG. 21B, CD3 expression was found on p24+ and p24– CD4 T cell populations from HIV-infected subjects PS05 and PS07. The mfi for p24+ and p24– cells are 87 and 85 for PS05, and 74 and 61 for PS07.

EXAMPLE 11

CD4 T cells supporting active HIV infection have higher levels of surface LFA-1 expression and LtxA has been shown to preferentially target activated CD4 T cells expressing higher levels of LFA-1, it was examined whether LtxA treatment can target the infected CD4 T cells and reduce the levels of viral DNA in the PBMCs of HIV-infected individuals.

PBMCs from two viremic HIV-infected subjects (PS05 with 38,165 vRNA copies/ml and CD4 count of 814 and PS14 with 21,815 vRNA copies/ml and CD4 count of 494) were treated with LtxA (7.8 µg/ml) for 20 hrs. The viral DNA and β-actin DNA were quantified by real time PCR with the specific primers. See FIG. 19A. Averages and standard deviation from 4-5 repeat experiments are presented.

Figure 19:
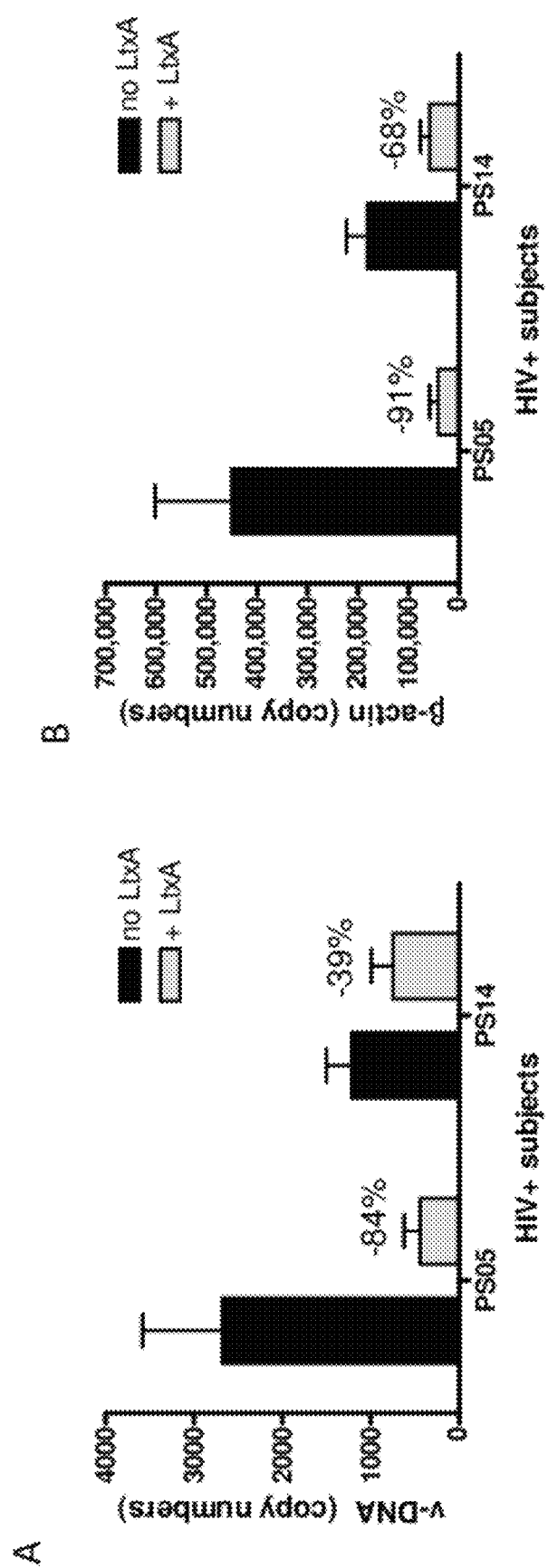
FIGS. 19A and 19B are a set of diagrams showing reduction of viral DNA in HIV-infected PBMCs due to LtxA cytotoxicity, where averages and standard deviation from 4-5 repeat experiments are presented.

As shown in FIG. 19A, 2682 and 1223 copies of viral DNA were initially detected in PBMCs of subjects PS05 (~2.5×10$^5$ cells) and PS014 (~1.2×10$^5$ cells), respectively, and LtxA treatment reduced the amounts of viral DNA by 84% and 39%. The reduction of viral DNA was accompanied respectively by 91% and 68% loss of PBMCs as indicated by β-actin measurement (FIG. 19B). The higher levels of cell loss relative to viral DNA reduction are not surprising, since not all cells sensitive to LtxA killing are infected by the virus. Indeed, HIV infection has been consistently associated with increased numbers of activated uninfected bystander CD4 and CD8 T lymphocytes (Giorgi, et al. 1993. *J Acquire Immune Defic Syndr* 6:904-912, and Hazenberg, et al. 2003. *Aids* 17:1881-1888).

In sum, the above study demonstrates that HIV-1 itself is capable of stimulating LFA-1 and converting it from an inactive state to an active conformation that allows a high affinity binding for the ICAM-1 ligand. It also discloses that LtxA is effective at removing cells bearing HIV-1 and reducing viral DNA loads due to its cytotoxic activity against activated LFA-1$^{hi+}$ cells that are most efficient to support productive HIV infection. These results were surprising since, unlike CD4 and the chemokine receptors, LFA-1 and ICAM-1 are not required for HIV infection.

The foregoing example and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

The invention claimed is:

1. A method of ameliorating symptoms of inflammatory autoimmune psoriasis in a mammalian subject in need thereof comprising administering to said subject a composition consisting of a pharmaceutically acceptable carrier and a therapeutically effective amount of an isolated leukotoxin set forth as SEQ ID NO: 1.

2. The method of claim 1, wherein the autoimmune psoriasis is characterized by leukocytes expressing upregulated and activated leukocyte function antigen-1 (LFA-1) on their surface.

3. The method of claim 1, wherein the leukotoxin is purified.

4. The method of any one of claims 1-3, wherein the leukotoxin is obtained from *Aggregatibacter actinomycetemcomitans*.

* * * * *

SEQUENCE LISTING

<160> NUMBER OF SEQ ID NOS: 6

<210> SEQ ID NO 1
<211> LENGTH: 1055
<212> TYPE: PRT
<213> ORGANISM: Aggregatibacter actinomycetemcomitans

<400> SEQUENCE: 1

```
Met Ala Thr Thr Ser Leu Leu Asn Thr Lys Gln Gln Ala Ala Gln Phe
1               5                   10                  15

Ala Asn Ser Val Ala Asp Arg Ala Lys Glu Asn Ile Asp Ala Ala Lys
            20                  25                  30

Glu Gln Leu Gln Lys Ala Leu Asp Lys Leu Gly Lys Thr Gly Lys Lys
        35                  40                  45

Leu Thr Leu Tyr Ile Lys Asn Tyr Lys Lys Gly Asn Gly Leu Thr Ala
    50                  55                  60

Leu Ile Lys Ala Ala Gln Lys Leu Gly Ile Glu Val Tyr His Glu Gly
65                  70                  75                  80

Lys Asp Gly Pro Ala Leu Thr Asn Gly Ile Leu Asn Thr Gly Lys Lys
                85                  90                  95

Leu Leu Gly Leu Thr Glu Arg Gly Leu Thr Leu Phe Ala Pro Glu Leu
            100                 105                 110

Asp Lys Trp Ile Gln Gly Asn Lys His Leu Ser Asn Ser Val Gly Ser
        115                 120                 125

Thr Gly Asn Leu Thr Lys Ala Ile Asp Lys Val Gln Ser Val Leu Gly
    130                 135                 140

Thr Leu Gln Ala Phe Leu Asn Thr Ala Phe Ser Gly Met Asp Leu Asp
145                 150                 155                 160

Ala Leu Ile Lys Ala Arg Gln Asn Gly Lys Asn Val Thr Asp Val Gln
                165                 170                 175

Leu Ala Lys Ala Ser Leu Asn Leu Ile Asn Glu Leu Ile Gly Thr Ile
            180                 185                 190

Ser Ser Ile Thr Asn Asn Val Asp Thr Phe Ser Lys Gln Leu Asn Lys
        195                 200                 205

Leu Gly Glu Ala Leu Gly Gln Val Lys His Phe Gly Ser Phe Gly Asp
    210                 215                 220
```

```
Lys Leu Lys Asn Leu Pro Lys Leu Gly Asn Leu Gly Lys Gly Leu Gly
225                 230                 235                 240

Ala Leu Ser Gly Val Leu Ser Ala Ile Ser Ala Leu Leu Leu Ala
            245                 250                 255

Asn Lys Asp Ala Asp Thr Ala Thr Lys Ala Ala Ala Ala Glu Leu
        260                 265                 270

Thr Asn Lys Val Leu Gly Asn Ile Gly Lys Ala Ile Thr Gln Tyr Leu
            275                 280                 285

Ile Ala Gln Arg Ala Ala Gly Leu Ser Thr Thr Gly Pro Val Ala
        290                 295                 300

Gly Leu Ile Ala Ser Val Val Ser Leu Ala Ile Ser Pro Leu Ser Phe
305                 310                 315                 320

Leu Gly Ile Ala Lys Gln Phe Asp Arg Ala Arg Met Leu Glu Glu Tyr
                325                 330                 335

Ser Lys Arg Phe Lys Lys Phe Gly Tyr Asn Gly Asp Ser Leu Leu Gly
            340                 345                 350

Gln Phe Tyr Lys Asn Thr Gly Ile Ala Asp Ala Ala Ile Thr Thr Ile
        355                 360                 365

Asn Thr Val Leu Ser Ala Ile Ala Ala Gly Val Gly Ala Ala Ser Ala
370                 375                 380

Gly Ser Leu Val Gly Ala Pro Ile Gly Leu Leu Val Ser Ala Ile Thr
385                 390                 395                 400

Ser Leu Ile Ser Gly Ile Leu Asp Ala Ser Lys Gln Ala Val Phe Glu
                405                 410                 415

His Ile Ala Asn Gln Leu Ala Asp Lys Ile Lys Ala Trp Glu Asn Lys
                420                 425                 430

Tyr Gly Lys Asn Tyr Phe Glu Asn Gly Tyr Asp Ala Arg His Ser Ala
            435                 440                 445

Phe Leu Glu Asp Ser Leu Lys Leu Phe Asn Glu Leu Arg Glu Lys Tyr
        450                 455                 460

Lys Thr Glu Asn Ile Leu Ser Ile Thr Gln Gln Gly Trp Asp Gln Arg
465                 470                 475                 480

Ile Gly Glu Leu Ala Gly Ile Thr Arg Asn Gly Asp Arg Ile Gln Ser
                485                 490                 495

Gly Lys Ala Tyr Val Asp Tyr Leu Lys Lys Gly Glu Glu Leu Ala Lys
            500                 505                 510

His Ser Asp Lys Phe Thr Lys Gln Ile Leu Asp Pro Ile Lys Gly Asn
        515                 520                 525

Ile Asp Leu Ser Gly Ile Lys Gly Ser Thr Thr Leu Thr Phe Leu Asn
530                 535                 540

Pro Leu Leu Thr Ala Gly Lys Glu Glu Arg Lys Thr Arg Gln Ser Gly
545                 550                 555                 560

Lys Tyr Glu Phe Ile Thr Glu Leu Lys Val Lys Gly Arg Thr Asp Trp
                565                 570                 575

Lys Val Lys Gly Val Pro Asn Ser Asn Gly Val Tyr Asp Phe Ser Asn
            580                 585                 590

Leu Ile Gln His Ala Val Thr Arg Asp Asn Lys Val Leu Glu Ala Arg
        595                 600                 605

Leu Ile Ala Asn Leu Gly Ala Lys Asp Asp Tyr Val Phe Val Gly Ser
610                 615                 620

Gly Ser Thr Ile Val Asn Ala Gly Asp Gly Tyr Asp Val Val Asp Tyr
625                 630                 635                 640
```

```
Ser Lys Gly Arg Thr Gly Ala Leu Thr Ile Asp Gly Arg Asn Ala Thr
                645                 650                 655
Lys Ala Gly Gln Tyr Lys Val Glu Arg Asp Leu Ser Gly Thr Gln Val
            660                 665                 670
Leu Gln Glu Thr Val Ser Lys Gln Glu Thr Lys Arg Gly Lys Val Thr
        675                 680                 685
Asp Leu Leu Glu Tyr Arg Asn Tyr Lys Leu Asp Tyr Tyr Tyr Thr Asn
    690                 695                 700
Lys Gly Phe Lys Ala His Asp Glu Leu Asn Ser Val Glu Glu Ile Ile
705                 710                 715                 720
Gly Ser Thr Leu Arg Asp Lys Phe Tyr Gly Ser Lys Phe Asn Asp Val
                725                 730                 735
Phe His Gly His Asp Gly Asp Leu Ile Tyr Gly Tyr Asp Gly Asp
            740                 745                 750
Asp Arg Leu Tyr Gly Asp Asn Gly Asn Asp Glu Ile His Gly Gly Gln
        755                 760                 765
Gly Asn Asp Lys Leu Tyr Gly Gly Ala Gly Asn Asp Arg Leu Phe Gly
    770                 775                 780
Glu Tyr Gly Asn Asn Tyr Leu Asp Gly Gly Glu Gly Asp Asp His Leu
785                 790                 795                 800
Glu Gly Gly Asn Gly Ser Asp Ile Leu Arg Gly Gly Ser Gly Asn Asp
                805                 810                 815
Lys Leu Phe Gly Asn Gln Gly Asp Asp Leu Leu Asp Gly Gly Glu Gly
            820                 825                 830
Asp Asp Gln Leu Ala Gly Gly Glu Gly Asn Asp Ile Tyr Val Tyr Arg
        835                 840                 845
Lys Glu Tyr Gly His His Thr Ile Thr Glu His Ser Gly Asp Lys Asp
    850                 855                 860
Lys Leu Ser Leu Ala Asn Ile Asn Leu Lys Asp Val Ser Phe Glu Arg
865                 870                 875                 880
Asn Gly Asn Asp Leu Leu Leu Lys Thr Asn Asn Arg Thr Ala Val Thr
                885                 890                 895
Phe Lys Gly Trp Phe Ser Lys Pro Asn Ser Ser Ala Gly Leu Asp Glu
            900                 905                 910
Tyr Gln Arg Lys Leu Leu Glu Tyr Ala Pro Glu Lys Asp Arg Ala Arg
        915                 920                 925
Leu Lys Arg Gln Phe Glu Leu Gln Arg Gly Lys Val Asp Lys Ser Leu
    930                 935                 940
Asn Asn Lys Val Glu Glu Ile Ile Gly Lys Asp Gly Glu Arg Ile Thr
945                 950                 955                 960
Ser Gln Asp Ile Asp Asn Leu Phe Asp Lys Ser Gly Asn Lys Lys Thr
                965                 970                 975
Ile Ser Pro Gln Glu Leu Ala Gly Leu Ile Lys Asn Lys Gly Lys Ser
            980                 985                 990
Ser Ser Leu Met Ser Ser Arg Ser Ser Ser Met Leu Thr Gln Lys
        995                 1000                1005
Ser Gly Leu Ser Asn Asp Ile Ser Arg Ile Ile Ser Ala Thr Ser
    1010                1015                1020
Gly Phe Gly Ser Ser Gly Lys Ala Leu Ser Ala Ser Pro Leu Gln
    1025                1030                1035
Thr Asn Asn Asn Phe Asn Ser Tyr Ala Asn Ser Leu Ala Thr Thr
    1040                1045                1050
Ala Ala
```

1055

<210> SEQ ID NO 2
<211> LENGTH: 3168
<212> TYPE: DNA
<213> ORGANISM: Aggregatibacter actinomycetemcomitans

<400> SEQUENCE: 2

| | | | | | |
|---|---|---|---|---|---|
| atggcaacta | cttcactgct | aaatacaaaa | cagcaagctg | cacagtttgc | aaattcagtt | 60 |
| gcagatagag | ctaaggaaaa | tattgatgct | gcaaaagaac | aattgcaaaa | ggcgttagat | 120 |
| aaattaggga | agacaggtaa | gaaattaact | ttatatatcc | ctaagaatta | caaaaaagga | 180 |
| aatggtctta | ctgcgcttat | aaaagcagca | cagaagttag | ggattgaagt | atatcatgaa | 240 |
| gggaaagacg | gcccggcatt | aactaatggt | atttttaaata | ctgggaaaaa | attacttggt | 300 |
| cttaccgaac | gaggtttaac | tttatttgct | ccggaattag | ataaatggat | tcaaggtaat | 360 |
| aaacatttaa | gtaattctgt | gggtagtact | ggaaatttga | caaaagcgat | agataaggtt | 420 |
| cagagtgttc | ttggtacgtt | acaagcgttt | ttgaacaccg | cattttcggg | catggattta | 480 |
| gatgccttaa | ttaaagcccg | tcaaaatggt | aaaaatgtaa | cagatgtaca | gctagcaaaa | 540 |
| gccagtctta | acctgattaa | tgaattgatt | ggtactattt | ctagcattac | aaataatgta | 600 |
| gatactttt | ctaaacaact | taataagtta | ggtgaagcac | taggacaagt | aaaacatttt | 660 |
| ggtagttttg | gagataaatt | aaagaattta | cctaagttag | gtaatcttgg | aaaaggttta | 720 |
| ggtgcattat | ccggtgtatt | gtcggctata | tcagcggctc | tattacttgc | aaataaagat | 780 |
| gctgatactg | caacgaaagc | agcggctgca | gctgaattga | caaataaagt | gctaggtaac | 840 |
| atcggtaaag | cgatcacaca | atacttgatt | gctcaacgtg | ctgcagcggg | gctttctact | 900 |
| acgggacctg | tcgcagggtt | aattgcctct | gtggtcagct | tggcaatcag | ccctttgtct | 960 |
| ttcctaggta | ttgcgaaaca | atttgatcgt | gcgagaatgc | ttgaggaata | ctcgaaacgc | 1020 |
| tttaagaaat | ttggttataa | cggcgatagt | ttacttggtc | aattctacaa | aaatacaggg | 1080 |
| atcgcagatg | ctgcgattac | aacgattaac | actgtattaa | gtgctattgc | agcaggggtt | 1140 |
| ggtgcagcct | ccgccggttc | tttagttggt | gcgccaatcg | gtttgttagt | gagtgcgatt | 1200 |
| accagcttaa | tttcaggaat | tcttgatgct | tctaaacaag | ccgttttga | acatatcgcg | 1260 |
| aatcagctcg | ccgataaaat | taaagcatgg | gagaataagt | acggtaagaa | ttactttgaa | 1320 |
| aatggctatg | atgcccgtca | ttccgccttc | ttggaagatt | cactaaaatt | atttaatgag | 1380 |
| ttacgtgaaa | aatataaaac | cgaaaatata | ttatctatca | ctcaacaagg | ttgggatcag | 1440 |
| cgcattggtg | aattagcagg | tatcactcgt | aatggagatc | gtattcaaag | tggtaaagct | 1500 |
| tatgtggatt | atttgaaaaa | gggtgaggag | cttgcaaagc | atagcgataa | attcactaaa | 1560 |
| cagattttag | atccaatcaa | aggtaatatt | gatcttcgg | gtataaaagg | ttctaccact | 1620 |
| ctaactttt | taaatccgtt | gttaaccgca | ggtaaggaag | aacggaaaac | acgtcagtca | 1680 |
| ggtaaatatg | aatttattac | tgaattaaaa | gtaaaaggac | gtaccgattg | gaaggtaaaa | 1740 |
| ggtgttccta | attctaatgg | tgtatatgat | ttttctaact | taattcaaca | tgccgttaca | 1800 |
| cgtgataata | aagttctaga | agcaagatta | attgctaatt | tgggtgctaa | agatgattat | 1860 |
| gttttttgtcg | gatccggttc | aacaatagtt | aatgctggag | acggttatga | tgtggtggac | 1920 |
| tatagtaaag | gtcgcaccgg | tgcattaaca | atcgacggtc | gtaatgctac | taaagccgga | 1980 |
| caatataagg | ttgaaagaga | tcttagcggt | actcaagtct | tgcaggaaac | cgtatcaaag | 2040 |
| caagaaacta | aacgagggaa | ggttaccgat | ctacttgaat | atcgtaacta | taaattagat | 2100 |

-continued

```
tactattata cgaataaggg ctttaaagct catgatgaat taaactcagt agaggaaatt    2160
atcggcagca cactacgtga taaattttat ggttctaaat ttaatgatgt tttccatggt    2220
cacgatggcg atgatttgat ttatggttat gatggcgatg atcgtttgta tggcgataat    2280
gggaatgacg aaaattcatgg cggccaaggt aatgataagc tctatggtgg tgccggtaac    2340
gataggctct ttggtgaata tggcaacaac tatcttgacg gtggagaagg cgacgaccac    2400
ttagagggag gcaatggttc cgatattcta agaggtggaa gtggcaatga taagttgttt    2460
ggaaaccaag gagatgattt acttgacggt ggagaaggcg atgaccaact tgccggtgga    2520
gaaggaaatg atatttatgt ttaccgtaaa gaatatgggc accacactat tacgaacat    2580 agcggtgata aagataaatt atcattagca aatatcaatc tcaaagatgt gtcatttgag    2640
cgtaacggca atgatctact attgaaaaca aataatagaa cagcagtaac atttaaagga    2700
tggtttagta aacctaattc atcggcagga ttagatgagt atcaaagaaa acttcttgaa    2760
tacgcacctg aaaaggatcg tgcacgactt aagagacaat ttgagttaca gcgaggtaaa    2820
gtcgacaaat cactcaataa taaagttgaa gaaattatcg gtaaagatgg ggagcggatt    2880
acttcgcaag acattgataa tctttttgat aagagtggga acaaaaagac aatttcacct    2940
caagagcttg ccggacttat taagaataaa ggtaagtcaa gtagccttat gtcttcttct    3000
cgttcgtcaa gtatgcttac acaaaagtcc ggtttgtcaa atgatattag tcgtattatt    3060
tcagcaacca gtggttttgg ttcatccggt aaagcgttat ccgcttcgcc attgcagacc    3120
aataataact ttaactctta cgcaaattcg ttagcaacta ctgcggcc                3168

<210> SEQ ID NO 3
<211> LENGTH: 28
<212> TYPE: DNA
<213> ORGANISM: Aggregatibacter actinomycetemcomitans

<400> SEQUENCE: 3
ataatccacc tatcccagta ggagaaat                                         28

<210> SEQ ID NO 4
<211> LENGTH: 28
<212> TYPE: DNA
<213> ORGANISM: Aggregatibacter actinomycetemcomitans

<400> SEQUENCE: 4
tttggtcctt gtcttatgtc cagaatgc                                         28

<210> SEQ ID NO 5
<211> LENGTH: 20
<212> TYPE: DNA
<213> ORGANISM: Aggregatibacter actinomycetemcomitans

<400> SEQUENCE: 5
ctccatcctg gcctcgctgt                                                  20

<210> SEQ ID NO 6
<211> LENGTH: 20
<212> TYPE: DNA
<213> ORGANISM: Aggregatibacter actinomycetemcomitans

<400> SEQUENCE: 6
caccttcacc gttccagttt                                                  20
```